(12) United States Patent
Koizumi

(10) Patent No.: US 7,906,639 B2
(45) Date of Patent: Mar. 15, 2011

(54) OLIGONUCLEOTIDES HAVING A 2'-O,4'-C-ETHYLENE NUCLEOTIDE IN THE THIRD POSITION OF THE 3'-END

(75) Inventor: Makoto Koizumi, Kawasaki (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/577,982

(22) PCT Filed: Nov. 4, 2004

(86) PCT No.: PCT/JP2004/016715
§ 371 (c)(1),
(2), (4) Date: May 2, 2006

(87) PCT Pub. No.: WO2005/045033
PCT Pub. Date: May 19, 2005

(65) Prior Publication Data
US 2007/0009897 A1    Jan. 11, 2007

(30) Foreign Application Priority Data

Nov. 7, 2003 (JP) ................................. 2003-378039
Apr. 16, 2004 (JP) ................................. 2004-121080

(51) Int. Cl.
*C07H 21/04* (2006.01)
*C12P 19/34* (2006.01)

(52) U.S. Cl. ...................................... 536/24.3; 435/91.2

(58) Field of Classification Search .................... None
See application file for complete search history.

(56) References Cited

U.S. PATENT DOCUMENTS 6,391,593 B1 *  5/2002  Weston et al. ............... 435/91.2
6,670,461 B1    12/2003  Nielsen et al.
(Continued)

FOREIGN PATENT DOCUMENTS

EP    1 013 661 A1    6/2000
(Continued)

OTHER PUBLICATIONS

Koizumi et al., Triplex formation with 2¢-O,4¢-C-ethylene-bridged nucleic acids (ENA) having C3'-endo conformation at physiological pH, Nucleic Acids Research, Jun. 15, 2003, vol. 31, No. 12 3267-3273.*

(Continued)

*Primary Examiner* — Mark Staples
(74) *Attorney, Agent, or Firm* — Holtz, Holtz, Goodman & Chick, P.C.

(57) ABSTRACT

The present invention relates to a method for detecting gene polymorphism by PCR, using, as a primer, an oligonucleotide, wherein the third nucleotide from the 3'-end thereof is a 2'-O,4'-C-ethylene nucleotide (ENA) unit, the other oligonucleotides are natural oligonucleotides, the 3'-end position thereof is a nucleotide complementary to the nucleotide of the reference sequence of a polymorphic sequence of a target gene, and the other positions are nucleotides complementary to the nucleotide sequence of the target gene, or an oligonucleotide, wherein the 3'-end of the nucleotide sequence thereof is a polymorphic position, the second nucleotide from the 3'-end thereof is a nucleotide having a base that is not complementary to a gene to be detected, and the third nucleotide from the 3'-end thereof is a 2'-O,4'-C-ethylene nucleotide (ENA) unit; oligonucleotides used in detection of gene polymorphism; and a kit for detecting gene polymorphism, comprising the above oligonucleotides.

41 Claims, 7 Drawing Sheets

U.S. PATENT DOCUMENTS

| | | | |
|---|---|---|---|
| 6,794,499 | B2 | 9/2004 | Wengel et al. |
| 7,034,133 | B2 | 4/2006 | Wengel et al. |
| 7,053,207 | B2 | 5/2006 | Wengel |
| 7,084,125 | B2 | 8/2006 | Wengel |
| 7,217,805 | B2 | 5/2007 | Imanishi et al. |
| 7,314,923 | B2 | 1/2008 | Kaneko et al. |
| 7,335,765 | B2 | 2/2008 | Kaneko et al. |
| 2001/0034023 | A1* | 10/2001 | Stanton et al. ............ 435/6 |
| 2002/0147332 | A1* | 10/2002 | Kaneko et al. ......... 536/26.1 |
| 2003/0134808 | A1 | 7/2003 | Wengel |
| 2003/0207841 | A1 | 11/2003 | Kaneko et al. |
| 2005/0287566 | A1 | 12/2005 | Wengel et al. |
| 2007/0117773 | A1 | 5/2007 | Koizumi et al. |

FOREIGN PATENT DOCUMENTS

| | | |
|---|---|---|
| JP | 10-304889 A | 11/1998 |
| JP | 2000-297097 A | 10/2000 |
| JP | 3420984 B2 | 4/2003 |
| WO | WO 99/14226 A2 | 3/1999 |

OTHER PUBLICATIONS

Braasch et al., Minireview, Locked nucleic acid (LNA): ¢ne-tuning the recognition of DNA and RNA, Chemistry & Biology 8 (2001) 1-7.*

Orum et al., Detection of the Factor V Leiden Mutation by Direct Allele-specific Hybridization of PCR Amplicons to Photoimmobilized Locked Nucleic Acids, Clinical Chemistry 45:11, 1898-1905 (1999).*

Leonid Kruglyak, "Prospects for whole-genome linkage disequilibrium mapping of common disease genes," *Nature Genetics*, vol. 22, Jun. 1999, pp. 139-144.

Henry A. Erlich et al., "Recent Advances in the Polymerase Chain Reaction," *Science*, Jun. 21, 1999, vol. 252, pp. 1643-1651.

Koji Morita et al., "Synthesis and Properties of 2'-O,4'-C-Ethylene-Bridged Nucleic Acids (ENA) as Effective Antisense Oligonucleotides," *Bioorganic & Medicinal Chemistry*, (2003), vol. 11, pp. 2211-2226.

Koji Morita et al., "2'-O,4'-C-Ethylene-Bridged Nucleic Acids (ENA): Highly Nuclease-Resistant and thermodynamically Stable Oligonucleotides for Antisense Drug," *Bioorganic & Medicinal Chemistry Letters*, (2002), vol. 12, pp. 73-76.

Kenneth J. Livak, "Allelic discrimination using fluorogenic probes and the 5' nuclease assay," *Genetic Analysis: Biomolecular Engineering*, (1999), vol. 14, pp. 143-149.

Timothy Morris et al., "Rapid Reverse Transcription-PCR Detection of Hepatitis C Virus RNA in Serum by Using the TagMan Fluorogenic Detection System," *Journal of Clinical Microbiology*, Dec. 1996, vol. 34, No. 12, pp. 2933-2936.

David Latorra et al., "Enhanced Allele-specific PCR Discrimination in SNP Genotyping Using 3'Locked Nucleic Acid (LNA) Primers," *Human Mutations*, (2003), 22:79-85.

Peter Mouritzen et al., "Single nucleotide polymorphism genotyping using locked nucleic acid (LNA™)," *Expert Rev. Mole. Diagn.*, (2003), 3, pp. 27-38.

David Latorra et al., "Design considerations and effects of LNA in PCR primers," *Molecular and Cellular Probes*, (2003), 17, pp. 253-259.

Makoto Koizumi et al., "SNP genotyping by allele-specific PCR using ENA primers," *Nucleic Acid Symposium Ser.*, (2005), No. 49, pp. 47-48.

Makoto Koizumi et al., "Triplex formation with 2'-O,4'-C-ethylene-bridged nucleic acids (ENA) having C3'-endo conformation at physiological pH," *Nucleic Acids Research*, (2003), vol. 13, No. 12, pp. 3267-3273.

Koji Morita et al., "2'-O,4'-C-Ethylene-Bridged Nucleic Acids (ENA): Highly Nuclease-Resistant and Thermodynamically Stable Oligonucleotides for Antisense Drug," *Bioorganic & Medicinal Chemistry Letters*, (2002) 12, pp. 73-76.

Masafumi Matsuo et al., "Study of Ability of Antisense ENA to Induce Exon Skipping of Dytrophin Gene," Kosei Rodosho Seishin Shinkei Shikkan Kenkyu Itakuhi ni yoru Kenkyu Hokokushu, Heisei 14 Nendo, Jul. 2003, p. 590.

Satoshi Obika, Daishu Nanbu, Yoshiyuki Hari, Jun-ichi Andoh, Ken-ichiro Morio, Takefumi Doi, and Takeshi Imanishi, "Stability and structural features of the duplexes containing nucleoside analogues with a fixed N-type conformation, 2'-O,4'-C-methyleneribonucleosides," *Tetrahedron Letters*, 39, (1998) 5401-5404.

Sanjay K. Singh, Poul Nielsen, Alexei A. Koshkin and Jesper Wengel, "LNA (locked nucleic acids): synthesis and high-affinity nucleic acid recognition," *Chemical Communication*, 1998, No. 4, pp. 455-456.

Alexei A. Koshkin, Sanjay K. Singh, Poul Nielsen, Vivek K. Rajwanshi, Ravindra Kumar, Michael Meldgaard, Cark Erik Olsen and Jesper Wengel, "LNA (Locked Nucleic Acids): Bicyclonucleoside Monomers, Oligomerisation, and Unprecedented Nucleic Acid Recognition," *Tetrahedron*, 54, (1998) 3607-3630.

Björn TEWS et al., "Application of the C4'-Alkylated Deoxyribose Primer System (CAPS) in Allele-Specific Real-Time PCR for Increased Selectivity in Discrimination of Single Nucleotide Sequence Variants," *Biol. Chem.*, (2003) vol. 384, pp. 1533-1541.

Makoto Koizumi et al., "Improvement of single nucleotide polymorphism genotyping by allele-specific PCR using primers modified with an ENA residue," *Analytical Biochemistry*, (2005), 340, pp. 287-294.

English-language International Preliminary Report on Patentability mailed on May 18, 2006 of International Application No. PCT/JP2004/016715 Applicant: Sankyo Company, Limited.

* cited by examiner

```
(KK/Nga,KK/Snk)                                    ACAT
(AKR)            ---ATCTGTCTACATATATATACACACA::T---

Primer      5'ATCTGTCTACATATATATACACACAT3'
            5'ATCTGTCTACATATATATACACACAC3'
```

US 7,906,639 B2

OLIGONUCLEOTIDES HAVING A 2'-O,4'-C-ETHYLENE NUCLEOTIDE IN THE THIRD POSITION OF THE 3'-END

This application is the United States national phase application of International Application PCT/JP2004/016715 filed Nov. 4, 2004.

TECHNICAL FIELD

The present invention relates to a method for detecting gene polymorphism by PCR using an oligonucleotide comprising an ENA unit, an oligonucleotide used in detection of gene polymorphism, and a kit for detecting gene polymorphism comprising the above oligonucleotide.

BACKGROUND ART

As a result of advances in pharmacogenomics, it is now possible to predict the effects or side effects of drugs in individual patients by gene diagnosis based on the relationship between gene polymorphism and drug effects, or between gene polymorphism and side effects. An example is the gene polymorphism of drug metabolizing enzymes. Examples of known drug metabolizing enzymes whose activity is increased or decreased by such polymorphism include cytochrome P4501A2, cytochrome P4502A6, cytochrome P4502C9, cytochrome P4502C19, cytochrome P4502D6, and cytochrome P4502E1. In addition, it has been reported that among a group of enzymes known as conjugation enzymes, such as thiopurine methyltransferase, N-acetyltransferase, UDP-glucuronosyltransferase, or glutathione S-transferase, such gene polymorphism exists, and that the activities of the above enzymes are decreased by such polymorphism ("SNP Idenshi Takei no Senryaku (Strategy of SNP Gene Polymorphism)", edited by Yusuke Nakamura, Nakayama Shoten, Jun. 5, 2000).

Moreover, by examining the relationship between gene polymorphism and diseases, the pre-diagnosis of several diseases or the determination of prognosis becomes possible. A large number of disease-associated genes discovered as a result of polymorphism analyses have been reported. Examples of such disease-associated genes, which have been reported, include: HLA, a causative gene of ulcerative colitis; TCRα, a causative gene of rheumatoid arthritis; APOE4, a causative gene of Alzheimer's disease; a dopamine D3 receptor, a causative gene of schizophrenia; tryptophan hydroxylase, a causative gene of manic-depressive psychosis; an angiotensin precursor, a causative gene of albuminuria; blood coagulation factor VII, a causative gene of myocardial infarct; and leptin, a causative gene of adiposis (Nature Genetics, 1999, Vol. 22, pp. 139-144).

Examples of methods for detecting gene polymorphism, which have been developed, include: the PCR-RFLP method, involving a combination of the polymerase chain reaction (PCR) method and cleavage with restriction enzymes (Science, 1991, Vol. 252, p. 1643-); the SSCP (single-strand conformation polymorphism) method, based on the principle that single-strand DNA and RNA having different sequences exhibit different electrophoretic mobility in polyacrylamide gels; and the AS-PCR (allele-specific PCR) method, based on the principle that mismatches existing at the 3'-end of an oligonucleotide primer inhibit elongation of the primer.

Since the PCR-RFLP method comprises a treatment with restriction enzymes for 3 to 24 hours in its test process, it is difficult to say that this is a rapid method. The SSCP method is excellent in that when one or several mutations exist in any part of the nucleotide sequence used as a test target, this method is able to detect such existence at high sensitivity. However, since the experimental conditions are strictly controlled to detect a subtle difference in mobility, this is extremely complicated, and furthermore, the position of the mutation cannot be identified by this method. In addition, in order to perform the SSCP method using actual analytes such as blood or tissues, it is necessary to prepare, in advance, a large amount of nucleic acid via cloning or the PCR method. Thus, this method is not suitable for efficiently testing a large number of analytes.

The AS-PCR method is a method that involves a modification of PCR. For this method it is not necessary to prepare in advance a large amount of nucleic acid. This method is based on the fact that an amplified product can be obtained only when primers having no mismatch around the 3'-ends thereof are used. This is a method suitable for efficiently testing a large number of analytes. However, there are cases where such an amplified product can be obtained in ordinary PCR, even when mismatches exist in primers. Thus, the above method has been problematic in terms of stringency.

Also, it has been reported that when the above AS-PCR method is modified, and when a primer having a nucleoside with a base that is not complementary to the target gene at the second position from the 3'-end is prepared, and the polymorphic portion to be detected is set at the 3'-end thereof, when compared with a primer having a nucleoside with a base complementary to the target gene at the second position from the 3'-end, detection of the polymorphic portion existing at the 3'-end is improved (Bioorganic & Medical Chemistry, 2003, Vol. 11, pp. 2211-2226). However, even when using this method, there are cases in which an amplified product can be obtained even if mismatch exists at the 3'-end of the primer. Accordingly, development of a method for detecting gene polymorphism at higher detection sensitivity is desired.

A 2'-O,4'-C-ethylene nucleotide (hereinafter referred to as an "ENA nucleotide" at times) is a non-natural nucleotide. An oligonucleotide into which such an ENA nucleotide has been introduced has high binding ability to complementary strand RNA (Japanese Patent No. 3420984 (Japanese Patent Laid-Open No. 12-297097) and Bioorganic & Medical Chemistry, 2003, Vol. 11, pp. 2211-2226). In addition, the ENA nucleotides are characterized in that they have a higher resistance to nuclease than LNA nucleotides (2'-O,4'-C-methylene nucleotide (Japanese Patent Laid-Open No. 10-304889), which are formed by crosslinking, with a methylene chain, an oxygen atom at the 2' position and a carbon atom at the 4' position of a sugar portion (Bioorganic & Medicinal Chemistry Letters, 2002, Vol. 12, pp. 73-76). However, it was not known if the use of ENA nucleotides in a primer would improve the sensitivity of AS-PCR.

As a result of studies directed towards solving the aforementioned problems with polymorphism detection methods, the present inventors have found that when an oligonucleotide used as a PCR primer has a polymorphic portion at the 3'-end thereof and the third position from the 3'-end is modified with ENA, the amount of an amplified product generated due to mismatches is decreased, and gene polymorphism can be detected with high precision. The inventors have further provided a kit for use in the above detection method.

Moreover, the present inventors have also found that when an oligonucleotide used as a PCR primer has a polymorphic portion at the 3'-end, a nucleotide having a base that is not complementary to a gene to be detected as the second nucleotide from the 3'-end, and the third position from the 3'-end is modified with ENA, the amount of an amplified product generated due to mismatches is decreased, and gene polymorphism can be detected with high precision. The inventors have further provided a kit for use in the above detection method, thereby completing the present invention.

DISCLOSURE OF THE INVENTION

It is an object of the present invention to provide a method for detecting gene polymorphism, an oligonucleotide for use in the above method, and a gene polymorphism detection kit comprising the above oligonucleotide.

The present invention relates to a method for detecting gene polymorphism, which utilizes a phenomenon whereby during the synthesis of a synthetic oligonucleotide primer having a nucleotide sequence complementary to the nucleotide sequence of nucleic acid used as a template, if the nucleotide at the 3'-end of the synthetic oligonucleotide primer is a nucleotide that is not complementary to the nucleotides of the template, elongation of the primer with DNA polymerase does not take place, but if a synthetic oligonucleotide primer is used that is completely complementary to the nucleotide sequence of the nucleic acid used as a template, elongation of the primer with DNA polymerase takes place.

More specifically, the present invention relates to a method for detecting gene polymorphism, characterized by using, as a primer, a synthetic oligonucleotide, wherein the 3'-end of the nucleotide sequence thereof is a polymorphic portion, and the third nucleotide from the 3'-end thereof is a 2'-O,4'-C-ethylene nucleotide (ENA) unit.

Moreover, the present invention relates to a method for detecting gene polymorphism, characterized by using, as a primer, a synthetic oligonucleotide, wherein the 3'-end of the nucleotide sequence thereof is a polymorphic portion, wherein the second nucleotide from the 3'-end thereof is a nucleotide having a base that is not complementary to a gene to be detected, and the third nucleotide from the 3'-end thereof is a 2'-O,4'-C-ethylene nucleotide (ENA) unit.

As specific means for achieving the object of the present invention, the present invention includes the following features:

(1) An oligonucleotide,
(a) wherein the third nucleotide from the 3'-end thereof is a 2'-O,4'-C-ethylene nucleotide (ENA) unit, and the other nucleotides are natural nucleotides; and
(b) wherein the oligonucleotide has a nucleotide complementary to the reference nucleotide of a target gene at the 3'-end position thereof, and has nucleotides complementary to the nucleotide sequence of the target gene at the other positions, or a salt thereof.

(2) An oligonucleotide,
(a) wherein the third nucleotide from the 3'-end thereof is a 2'-O,4'-C-ethylene nucleotide (ENA) unit, and the other nucleotides are natural nucleotides; and
(b) wherein the oligonucleotide has a nucleotide complementary to the mutant nucleotide of a target gene at the 3'-end position thereof, and has nucleotides complementary to the nucleotide sequence of the target gene at the other positions, or a salt thereof.

(3) An oligonucleotide,
(a) wherein the 3'-end nucleotide thereof is a nucleotide complementary to the reference nucleotide of a target gene;
(b) wherein the second nucleotide from the 3'-end thereof (when the nucleotide at the 3'-end is defined as the first nucleotide) is a nucleotide that is not complementary to the nucleotide of a reference gene;
(c) wherein the oligonucleotide has nucleotides complementary to the nucleotides of the target gene at the other positions; and
(d) wherein the third nucleotide from the 3'-end thereof (when the nucleotide at the 3'-end is defined as the first nucleotide) is a 2'-O,4'-C-ethylene nucleotide (ENA) unit, and the other nucleotides are natural nucleotides, or a salt thereof.

(4) An oligonucleotide,
(a) wherein the 3'-end nucleotide thereof is a nucleotide complementary to the mutant nucleotide of a target gene;
(b) wherein the second nucleotide from the 3'-end thereof (when the nucleotide at the 3'-end is defined as the first nucleotide) is a nucleotide that is not complementary to the nucleotide of a reference gene;
(c) wherein the oligonucleotide has nucleotides complementary to the nucleotides of the target gene at the other positions; and
(d) wherein the third nucleotide from the 3'-end thereof (when the nucleotide at the 3'-end is defined as the first nucleotide) is a 2'-O,4'-C-ethylene nucleotide (ENA) unit, and the other nucleotides are natural nucleotides, or a salt thereof.

(5) An oligonucleotide or a salt thereof according to any one of (1) to (4) above, characterized by having a base length of 18 to 25 bases.

(6) A method for detecting gene polymorphism, characterized by using an oligonucleotide according to any one of (1) to (5) above.

(7) A method for determining the nucleotide sequence of a genetically polymorphic sequence, characterized by using an oligonucleotide according to any one of (1) to (5) above.

(8) A method for detecting gene polymorphism, comprising the following steps (a) and (b):
(a) a step of performing PCR with a nucleic acid comprising a genetically polymorphic sequence as a template using an oligonucleotide according to any one of (1) to (5) above and an oligonucleotide capable of amplifying a sequence of interest together with the aforementioned oligonucleotide in the PCR; and
(b) a step of determining the presence or absence of gene polymorphism in the nucleic acid based on whether or not a reaction product can be generated in step (a).

(9) A method for determining the nucleotide sequence of a genetically polymorphic sequence, comprising the following steps (a) and (b):
(a) a step of performing PCR with a nucleic acid comprising a genetically polymorphic sequence as a template using an oligonucleotide according to any one of (1) to (5) above and an oligonucleotide capable of amplifying a sequence of interest together with the aforementioned oligonucleotide in the PCR; and
(b) a step of determining the nucleotide sequence of a genetically polymorphic sequence in the nucleic acid based on whether or not a reaction product can be generated in step (a).

(10) A method according to (8) or (9), characterized by using, for detection of the presence or absence of generation of a reaction product, one or more method selected from the group consisting of electrophoresis, TaqMan PCR, and a MALDI-TOF/MS method.

(11) A method according to any one of (6) to (10) above, characterized in that the gene polymorphism is a single nucleotide polymorphism.

(12) A kit for detecting gene polymorphism, which comprises the following (a) to (d):
(a) an oligonucleotide, wherein the third nucleotide from the 3'-end thereof is a 2'-O,4'-C-ethylene nucleotide (ENA) unit, the other nucleotides are natural nucleotides, the 3'-end nucleotide thereof is a nucleotide complementary to the reference nucleotide of a target gene, and at the other positions the nucleotides are complementary to the nucleotide sequence of the target gene;
(b) an oligonucleotide capable of amplifying a sequence of interest, together with the oligonucleotide described in (a) above;
(c) DNA polymerase; and
(d) a PCR buffer.
(13) A kit for detecting gene polymorphism, comprising the following (a) to (d):
(a) an oligonucleotide, wherein the third nucleotide from the 3'-end thereof is a 2'-O,4'-C-ethylene nucleotide (ENA) unit, the other nucleotides are natural nucleotides, the 3'-end nucleotide thereof is a nucleotide complementary to the mutant nucleotide of a target gene, and at the other positions the nucleotides are complementary to the nucleotide sequence of the target gene;
(b) a primer capable of amplifying a portion of a sequence of interest, together with the oligonucleotide described in (a) above;
(c) DNA polymerase; and
(d) a PCR buffer.
(14) A kit for detecting gene polymorphism, comprising the following (a) to (e):
(a) an oligonucleotide, wherein the third nucleotide from the 3'-end thereof is a 2'-O,4'-C-ethylene nucleotide (ENA) unit, the other nucleotides are natural nucleotides, the 3'-end nucleotide thereof is a nucleotide complementary to the reference nucleotide of a target gene, and at the other positions the nucleotides are complementary to the nucleotide sequence of the target gene;
(b) an oligonucleotide, wherein the third nucleotide from the 3'-end thereof is a 2'-O,4'-C-ethylene nucleotide (ENA) unit, the other nucleotides are natural nucleotides, the 3'-end nucleotide thereof is a nucleotide complementary to the mutant nucleotide of a target gene, and at the other positions the nucleotides are complementary to the nucleotide sequence of the target gene;
(c) an oligonucleotide capable of amplifying a sequence of interest, together with the oligonucleotide described in (a) or (b) above;
(d) DNA polymerase; and
(e) a PCR buffer.
(15) A kit for detecting gene polymorphism, comprising the following (a) to (d):
(a) an oligonucleotide,
  (i) wherein the 3'-end nucleotide thereof is a nucleotide complementary to the reference nucleotide of a target gene;
  (ii) wherein the second nucleotide from the 3'-end thereof (when the nucleotide at the 3'-end is defined as the first nucleotide) is a nucleotide that is not complementary to the nucleotide of a reference gene;
  (iii) wherein the oligonucleotide has nucleotides complementary to the nucleotides of the target gene at the other positions; and
  (iv) wherein the third nucleotide from the 3'-end thereof (when the nucleotide at the 3'-end is defined as the first nucleotide) is a 2'-O,4'-C-ethylene nucleotide (ENA) unit, and the other nucleotides are natural nucleotides, or a salt thereof;
(b) an oligonucleotide capable of amplifying a sequence of interest, together with the oligonucleotide described in (a) above;
(c) DNA polymerase; and (d) a PCR buffer.
(16) A kit for detecting gene polymorphism, comprising the following (a) to (d):
(a) an oligonucleotide,
  (i) wherein the 3'-end nucleotide thereof is a nucleotide complementary to the mutant nucleotide of a target gene;
  (ii) wherein the second nucleotide from the 3'-end thereof (when the nucleotide at the 3'-end is defined as the first nucleotide) is a nucleotide that is not complementary to the nucleotide of a reference gene;
  (iii) wherein the oligonucleotide has nucleotides complementary to the nucleotides of the target gene at the other positions; and
  (iv) wherein the third nucleotide from the 3'-end thereof (when the nucleotide at the 3'-end is defined as the first nucleotide) is a 2'-O,4'-C-ethylene nucleotide (ENA) unit, and the other nucleotides are natural nucleotides, or a salt thereof;
(b) an oligonucleotide capable of amplifying a sequence of interest, together with the oligonucleotide described in (a) above;
(c) DNA polymerase; and
(d) a PCR buffer.
(17) A kit for detecting gene polymorphism, comprising the following (a) to (e):
(a) an oligonucleotide,
  (i) wherein the 3'-end nucleotide thereof is a nucleotide complementary to the reference nucleotide of a target gene;
  (ii) wherein the second nucleotide from the 3'-end thereof (when the nucleotide at the 3'-end is defined as the first nucleotide) is a nucleotide that is not complementary to the nucleotide of a reference gene;
  (iii) wherein the oligonucleotide has nucleotides complementary to the nucleotides of the target gene at the other positions; and
  (iv) wherein the third nucleotide from the 3'-end thereof (the nucleotide at the 3'-end is defined as the first nucleotide) is a 2'-O,4'-C-ethylene nucleotide (ENA) unit, and the other nucleotides are natural nucleotides, or a salt thereof;
(b) an oligonucleotide,
  (i) wherein the 3'-end nucleotide thereof is a nucleotide complementary to the mutant nucleotide of a target gene;
  (ii) wherein the second nucleotide from the 3'-end thereof (when the nucleotide at the 3'-end is defined as the first nucleotide) is a nucleotide that is not complementary to the nucleotide of a reference gene;
  (iii) wherein the oligonucleotide has nucleotides complementary to the nucleotides of the target gene at the other positions; and
  (iv) wherein the third nucleotide from the 3'-end thereof (when the nucleotide at the 3'-end is defined as the first nucleotide) is a 2'-O,4'-C-ethylene nucleotide (ENA) unit, and wherein the other nucleotides are natural nucleotides, or a salt thereof;
(c) an oligonucleotide capable of amplifying a sequence of interest, together with the oligonucleotide described in (a) or (b) above;
(d) DNA polymerase; and
(e) a PCR buffer.
(18) A kit for detecting gene polymorphism according to any one of (12) to (17) above, characterized in that the oligonucleotide, and the oligonucleotide capable of amplifying a sequence of interest together with the aforementioned oligonucleotide, each have a base length of 18 to 25 bases.
(19) A kit according to any one of (12) to (18) above, characterized in that the gene polymorphism is a single nucleotide polymorphism.

The principle of the method for detecting gene polymorphism of the present invention is as follows:
(1) The 3'-end of a primer is directed to the polymorphic portion of a sequence in which gene polymorphism is intended to be detected (sequence of interest), and the third nucleotide from the 3'-end of the primer is modified with a 2'-O,4'-C-ethylene nucleotide (ENA) unit. When this primer and nucleic acid containing a nucleotide sequence which is the gene polymorphism detection target are reacted with a mixture of nucleic acid synthesizing enzymes in a reaction solution, if the 3'-end of the primer matches (i.e. the base is complementary), a nucleic acid synthesis reaction takes place. In contrast, if the 3'-end does not match, a nucleic acid synthesis reaction does not take place. Utilizing the difference between the situation in which a nucleic acid synthesis reaction takes place when the 3'-end matches and the situation when a reaction does not take place when the 3'-end does not match, mutation can be detected in a nucleotide sequence. This principle is explained in FIGS. 1 and 2.

FIG. 1 shows the situation when there is no mutation (polymorphism) in a nucleic acid sequence. (i) is a template nucleic acid of a target in which it is intended to examine mutation (polymorphism) in the nucleic acid sequence, and it has the sequence 3'-ATGC-5' as a nucleotide sequence portion thereof. This template nucleic acid is annealed with oligonucleotide (ii) in which the third position from the 3'-end thereof has been modified with ENA (a 2'-O,4'-C-ethylene-5-methyluridine unit is represented by eT), so as to form a double strand. In this case, at least the 3'-end of the nucleotide sequence of (ii) has a structure that is complementary to the corresponding base, and (ii) and (i) form a double strand. The 3'-end portion of oligonucleotide (ii) forming such a double strand is recognized by nucleic acid synthesizing enzyme (iii), and the nucleic acid synthesis reaction is continued. Specific nucleotide sequences shown in the figure are used for explanation, and thus, it does not mean that the present invention is effective only for such nucleotide sequences.

FIG. 2 shows a case where there is mutation (polymorphism) in a nucleic acid sequence. (i) is a template nucleic acid of a target in which it is intended to examine mutation (polymorphism) in the nucleic acid sequence, and it has the sequence 3'-ATAC-5' as a nucleotide sequence portion thereof. This template nucleic acid is annealed with oligonucleotide (ii) in which the third position from the 3'-end thereof has been modified with ENA (a 2'-O,4'-C-ethylene-5-methyluridine unit is represented by eT), so as to form a double strand. In this case, at least the 3'-end of the nucleotide sequence of (ii) does not have a structure that is complementary to the corresponding base, and C at the 3'-end of (ii) and A of (i) do not form a Watson-Crick base pair. The 3'-end portion of oligonucleotide (ii) that does not form a Watson-Crick base pair cannot be recognized by the nucleic acid synthesizing enzyme (iii), and the nucleic acid synthesis reaction cannot be continued. Specific nucleotide sequences shown in the figure are used for explanation, and thus, it does not mean that the present invention is effective for only for such nucleotide sequences.

Another principle of the method for detecting gene polymorphism of the present invention is as follows:

(2) The 3'-end of a primer is directed to the polymorphic portion of a sequence in which gene polymorphism is intended to be detected (sequence of interest), and a nucleotide having a base that is not complementary to the gene to be detected is used as the second nucleotide from the 3'-end of the primer. In addition, the third nucleotide from the 3'-end of the primer is modified with an ENA unit. When this primer, a nucleic acid containing a nucleotide sequence as a gene polymorphism detection target and an oligonucleotide capable of amplifying a sequence of interest together with the above primer in PCR are reacted with a mixture of nucleic acid synthesizing enzymes in a reaction solution, if the 3'-end of the primer matches (i.e. the base is complementary), a nucleic acid synthesis reaction takes place, and the gene is amplified. In contrast, if the 3'-end does not match, a nucleic acid synthesis reaction does not take place, and the gene is not amplified. Utilizing the difference between the situation in which a nucleic acid synthesis reaction takes place when the base at the 3'-end is complementary and the situation when a reaction does not take place when the base at the 3'-end is not complementary, mutation can be detected in a nucleotide sequence. This principle is explained in FIGS. 3 and 4.

FIG. 3 shows a situation in which there is no mutation (polymorphism) in a nucleic acid sequence. (i) is a template nucleic acid of a target in which it is intended to examine mutation (polymorphism) in the nucleic acid sequence, and it has the sequence 3'-ATGC-5' as a nucleotide sequence portion thereof. (ii) is a primer. In this primer, the second nucleoside from the 3'-end is a nucleoside that is not complementary to the gene to be detected (guanine (G) in the figure), and the other nucleosides are complementary to the gene to be detected. In addition, the third position from the 3'-end is an oligonucleotide modified with an ENA (a 2'-O,4'-C-ethylene-5-methyluridine unit is represented by eT). In this situation, the nucleotide sequence of (ii) other than the second position from the 3'-end thereof is complementary to the corresponding nucleotide sequence of (i). Although there is a mismatch at the second position from the 3'-end of the nucleotide sequence of (ii), the template nucleic acid is annealed with the polymorphism detection primer, so as to form a double strand. The 3'-end portion of oligonucleotide (ii) forming such a complementary strand is recognized by the nucleic acid synthesizing enzyme (iii), and the nucleic acid synthesis reaction is continued.

Specific nucleotide sequences shown in the figure are used for explanation only, and thus, it does not mean that the present invention is effective only for such nucleotide sequences.

FIG. 4 shows the situation in which there is a mutation (polymorphism) in a nucleic acid sequence. (i) is a template nucleic acid of a target in which it is intended to examine mutation (polymorphism) in the nucleic acid sequence and it has the sequence 3'-ATAC-5' as a nucleotide sequence portion thereof. (ii) is a primer. In this primer, the nucleoside at the 3'-end and the second nucleoside from the 3'-end are nucleosides that are not complementary to those of the gene to be detected (guanine (G) in the figure), and other nucleosides are complementary to those of the gene to be detected. In addition, the third position from the 3'-end is an oligonucleotide modified with an ENA (a 2'-O,4'-C-ethylene-5-methyluridine unit is represented by eT). In this situation, the nucleoside at the 3'-end and the nucleoside at the second position from the 3'-end in the nucleotide sequence of (ii) are not complementary to the corresponding nucleosides. Thus, the 3'-end portion of (ii) does not form a Watson-Crick base pair. The 3'-end portion of oligonucleotide (ii) that does not form a Watson-Crick base pair cannot be recognized by the nucleic acid synthesizing enzyme (iii), and thus the nucleic acid synthesis reaction does not progress.

Specific nucleotide sequences shown in the figure are used for explanation only, and thus, it does not mean that the present invention is effective only for such nucleotide sequences.

The present invention provides a novel method for detecting gene polymorphism. Using a method for detecting gene polymorphism of the present invention, it is now possible to detect polymorphism more precisely than when using a natural oligonucleotide.

Moreover, the present invention also provides an oligonucleotide for use in detection of gene polymorphism and a kit for detecting gene polymorphism, which comprises the above oligonucleotide, which can be used for the above method.

1. Explanation of Terms

The term "gene polymorphism" is used in the present specification to mean a certain gene locus, which comprises (a) substitution of a single base with another base (single nucleotide polymorphism (SNP)) and/or (b) deletion or insertion of one to several tens of bases (wherein the number of bases is several thousands of bases in some cases) (insertion/deletion polymorphism). In the present specification, single nucleotide polymorphism is also referred to as SNP, and it means a difference of a single base in nucleotide sequences between individuals.

It is known that alternative nucleotides may be present at a single nucleotide polymorphism position (for example adenine or guanine, thymine or cytosine, etc). The ratio of these variants differs depending on the target gene. The term "target gene" is used in the present specification to mean a gene used as a target for gene polymorphism.

In the present specification, a sequence containing a nucleotide with a high frequency of occurrence among alternative variants in a single nucleotide polymorphic site of a target gene is defined as a reference sequence, and the nucleotide in the single nucleotide polymorphic site in such a reference sequence is defined as a reference nucleotide. On the other hand, a sequence containing a nucleotide with a low frequency of occurrence is defined as a mutant sequence, and the nucleotide in the single nucleotide polymorphic site in such a mutant sequence is defined as a mutant nucleotide.

Moreover, when the polymorphism is a deletion polymorphism, a sequence having no deletion is defined as the reference sequence, and a sequence having a deletion is defined as the mutant sequence.

Furthermore, when the polymorphism is an insertion polymorphism, a sequence having no insertion is defined as the reference sequence, and a sequence having an insertion is defined as the mutant sequence.

In the present specification, the expression "have polymorphism" is used to mean that a sequence comprising a polymorphism of interest in a target gene has a mutant sequence, and the expression "does not have polymorphism" is used to mean that a sequence comprising a polymorphism of interest in a target gene is a reference sequence.

In the present specification, the term "natural nucleotide" includes adenine nucleotide, guanine nucleotide, cytosine nucleotide, uracil nucleotide, and thymine nucleotide. In addition, the term "natural oligonucleotide" is used to mean an oligonucleotide composed of natural nucleotides such as adenine nucleotide, guanine nucleotide, cytosine nucleotide, uracil nucleotide, or thymine nucleotide.

In the present specification, adenine nucleotide may be represented by $A^p$, guanine nucleotide is represented by $G^p$, cytosine nucleotide is represented by $C^p$, and thymine nucleotide is represented by $T^p$. Moreover, with regard to the nucleotide at the 3'-end of a natural oligonucleotide, adenine nucleoside is represented by $A^r$, guanine nucleoside is represented by $G^r$, cytosine nucleoside is represented by $C^r$, and thymine nucleoside may be represented by $T^r$.

The structural formulas of natural nucleotides are shown below.

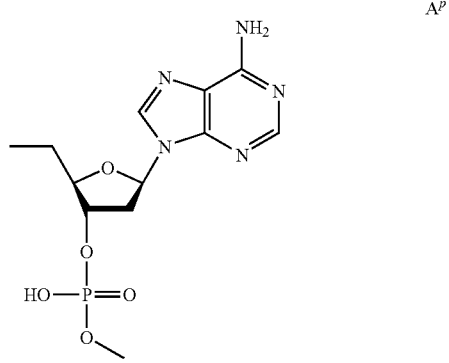

$A^p$

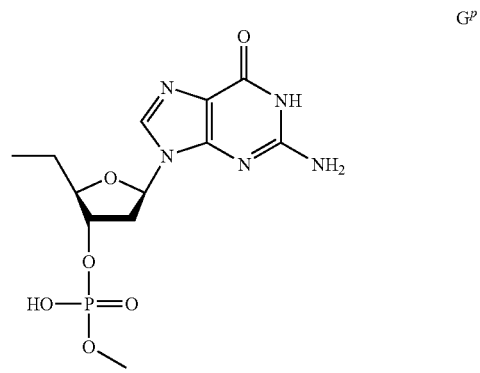

$G^p$

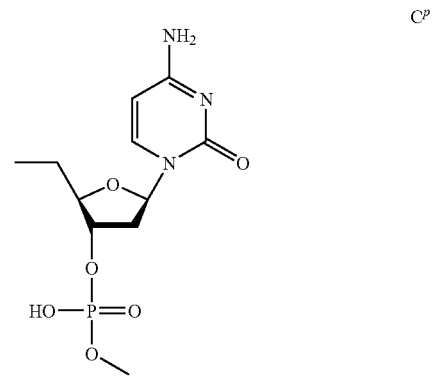

$C^p$

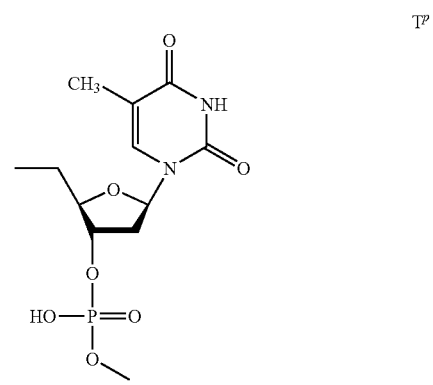

$T^p$

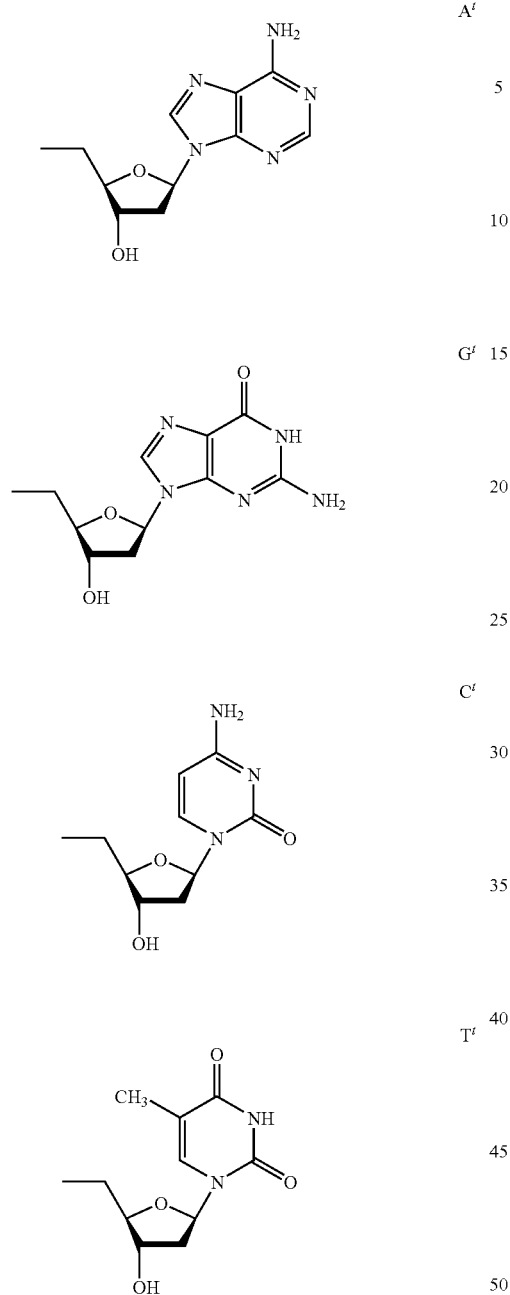

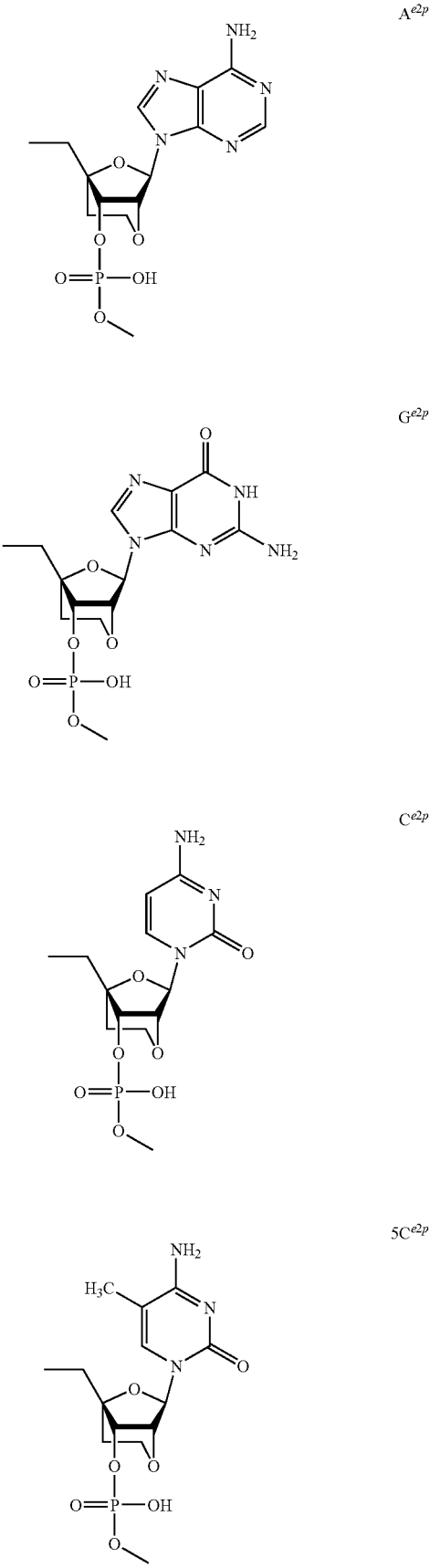

In the present specification, the term "ENA nucleotide" (hereinafter also referred to as "ENA") is used to mean a nucleotide, which is formed by crosslinking the oxygen atom at the 2' position of a sugar portion and the carbon atom at the 4' position thereof using an ethylene chain (refer to Japanese Patent No. 3420984).

In the present specification, each of the terms "2'-O,4'-C-ethylene nucleotide unit" and "ENA unit" is used to mean $A^{e2p}$, $G^{e2p}$, $C^{e2p}$, $5C^{e2p}$ or $T^{e2p}$, or when the 3'-end of an oligonucleotide has such a unit, or when ENA is treated as a nucleoside, it means any group selected from among $C^{e2t}$, $5C^{e2t}$, and $T^{e2t}$. The structures thereof are shown below. Further, the structure of $C^{e1p}$ is also shown as an LNA unit below.

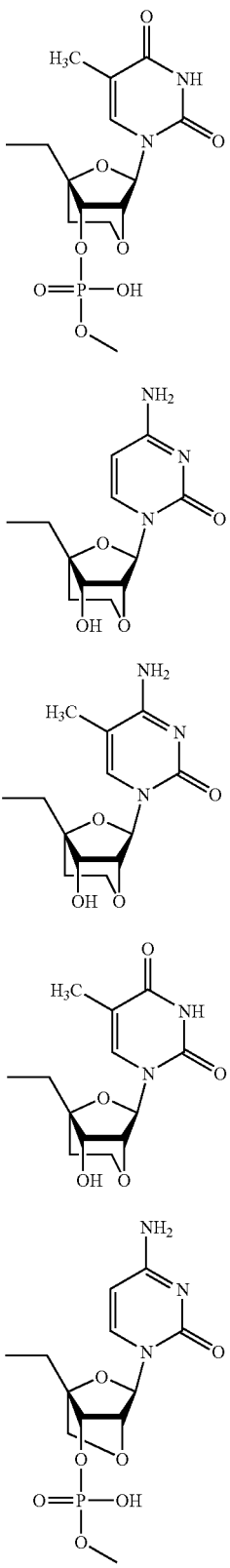

nucleotide base pairs complementary to each other are adenine and thymine, guanine and cytosine, or adenine and uracil.

The term "salt thereof" is used in the present specification to mean a salt, into which a compound of the present invention can be converted. Preferred examples of such a salt include: alkali metal salts such as a sodium salt, a potassium salt, or a lithium salt; alkali-earth metal salts such as a calcium salt or a magnesium salt; metal salts such as an aluminum salt, an iron salt, a zinc salt, a copper salt, a nickel salt, or a cobalt salt; inorganic salts such as an ammonium salt; amine salts including organic salts such as t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzyl-phenethylamine salt, a piperazine salt, a tetramethylammonium salt, or a tris(hydroxymethyl)aminomethane salt; halogenated hydroacid salts such as hydrofluoride, hydrochloride, hydrobromate, or hydroiodide; inorganic acid salts such as nitrate, perchlorate, sulfate, or phosphate; lower alkanesulfonates such as methanesulfonate, trifluoromethanesulfonate, or ethanesulfonate; arylsulfonates such as benzenesulfonate or p-toluenesulfonate; organic acid salts such as acetate, malate, fumarate, succinate, citrate, tartrate, oxalate, or maleate; and amino acid salts such as a glycine salt, a lysine salt, an arginine salt, an ornithine salt, a glutamate salt, or aspartate salt.

A compound of the present invention and a salt thereof can also be present in the form of a hydrate. The present invention includes such hydrates.

2. Analyte

As an analyte used as a target wherein gene polymorphism is to be detected in the present invention, a sample containing nucleic acid can be used. An example of such nucleic acid is genomic DNA, but examples are not limited thereto.

For example, in order to detect human gene polymorphism, an analyte containing human genomic DNA can be used. In order to detect mouse gene polymorphism, mouse genomic DNA can be used. Such genomic DNA can be obtained by methods known to persons skilled in the art. Hereafter, human genomic DNA will be used as an example. However, genomic DNA derived from other organisms can also be obtained in the same manner.

As material for obtaining genomic DNA, all types of cells (excluding germ cells), tissues, organs, etc. collected from a subject, can be used. Preferred examples of such materials include leukocytes or monocytes separated from peripheral blood, the most preferred example being leukocytes. Such materials can be collected by methods commonly used in clinical tests.

When leukocytes are used, the leukocytes are first separated from the peripheral blood collected from a subject by well known methods. Subsequently, proteinase K and sodium dodecyl sulfate (SDS) are added to the leukocytes so obtained to digest and denature proteins, this is followed by phenol/chloroform extraction to obtain genomic DNA (including RNA). RNA is removed with RNase, as necessary. However, the present invention is not limited to the aforementioned method. In order to extract genomic DNA from a sample containing human genomic DNA, methods publicly known in the technical field of the present invention are preferred, such as methods described in publications (refer to Sambrook, J. et al. (1989): "Molecular Cloning: A Laboratory Manual (2nd Ed.)" Cold Spring Harbor Laboratory, NY, for example), or a method using a commercially available DNA extraction kit.

The term "complementary nucleotide" is used in the present specification to mean a nucleotide with a base portion complementary to that of another nucleotide. Specifically, the The purity of an analyte containing DNA is not particularly limited, as long as it can be used for PCR. A crude extract, a purified product, etc. obtained from a sample can be used.

3. Selection of Target Gene

Any gene can be used as a target for detection of wherein gene polymorphism, provided that at least a nucleotide sequence portion thereof is already known and polymorphism exists in that portion. Examples of such target genes include known drug metabolizing genes associated with drug effects, or the side effects of drugs, such as cytochrome P4501A2, cytochrome P4502A6, cytochrome P4502C9, cytochrome P4502C19, cytochrome P4502D6, or cytochrome P4502E1. In addition, further examples include thiopurine methyltransferase, N-acetyltransferase, UDP-glucuronosyltransferase, glutathione S-transferase, and disease-associated genes such as HLA that is a causative gene of ulcerative colitis, TCRα that is a causative gene of rheumatoid arthritis, APOE4 that is a causative gene of Alzheimer's disease, a dopamine D3 receptor that is a causative gene of schizophrenia, tryptophan hydroxylase that is a causative gene of manic-depressive psychosis, an angiotensin precursor that is a causative gene of albuminuria, blood coagulation factor VII that is a causative gene of myocardial infarct, or leptin that is a causative gene of adiposis. A further example is human prothrombin.

When mouse genomic DNA is used as an analyte, examples of polymorphism include polymorphism of a mouse angiopoietin-like 3 gene promoter and deletion polymorphism.

The position of the polymorphism in a gene may be any of: a translated region, a nontranslated region, a regulatory region such as a promoter, or an intron, and other regions.

4. Oligonucleotide Primer

The following oligonucleotides can be synthesized using an automated nucleic acid synthesizer.

Natural oligonucleotides can be synthesized using natural phosphoramidite. A 2'-O,4'-C-ethylene nucleotide can be synthesized using the following compounds:
(5'-O-dimethoxytrityl-2'-O,4'-C-ethylene-6-N-benzoyladenosine-3'-O-(2-cyanoethyl N,N-diisopropyl)phosphoramidite (Example 14 of Japanese Patent No. 3420984),
5'-O-dimethoxytrityl-2'-O,4'-C-ethylene-2-N-isobutyrylguanosine-3'-O-(2-cyanoethyl N,N-diisopropyl) phosphoramidite (Example 27),
5'-O-dimethoxytrityl-2'-O,4'-C-ethylene-4-N-benzoylcytidine-3'-O-(2-cyanoethyl N,N-diisopropyl)phosphoramidite (Example 5),
5'-O-dimethoxytrityl-2'-O,4'-C-ethylene-4-N-benzoyl-5-methylcytidine-3'-O-(2-cyanoethyl N,N-diisopropyl) phosphoramidite (Example 22), and
5'-O-dimethoxytrityl-2'-O,4'-C-ethylene-5-methyluridine-3'-O-(2-cyanoethyl N,N-diisopropyl)phosphoramidite (Example 9).

(1) Oligonucleotides Used in Detection of Gene Polymorphism (1)-1 Oligonucleotides used in detection of gene polymorphism in the present invention include the following (a) and (b):

(a) an oligonucleotide having a nucleotide sequence complementary to a reference sequence,
(i) wherein the third nucleotide from the 3'-end thereof (when the nucleotide at the 3'-end is defined as the first nucleotide) is a 2'-O,4'-C-ethylene nucleotide (ENA) unit, and the other nucleotides are natural nucleotides;
(ii) wherein the oligonucleotide has a nucleotide complementary to the reference nucleotide of a target gene at the 3'-end position thereof, and has nucleotides complementary to the nucleotide sequence of the target gene at the other positions; and
(iii) wherein the length of the oligonucleotide primer is not particularly limited, as long as it is able to amplify nucleic acid in PCR, but the length is preferably 15 to 40 nucleotides, more preferably 18 to 35 nucleotides, and still more preferably 18 to 25 nucleotides.

Hereinafter, an oligonucleotide having the aforementioned characteristics is called an "X-PRIMER."

(b) an oligonucleotide having a nucleotide sequence complementary to a mutant sequence,
(i) wherein the third nucleotide from the 3'-end thereof (when the nucleotide at the 3'-end is defined as the first nucleotide) is a 2'-O,4'-C-ethylene nucleotide (ENA) unit, and the other nucleotides are natural nucleotides;
(ii) wherein the oligonucleotide has a nucleotide complementary to the mutant nucleotide of a target gene at the 3'-end position thereof, and has nucleotides complementary to the nucleotide sequence of the target gene at the other positions; and
(iii) wherein the length of the oligonucleotide thereof is not particularly limited, as long as it is able to amplify a nucleic acid in PCR, but the length is preferably 15 to 40 nucleotides, more preferably 18 to 35 nucleotides, and still more preferably 18 to 25 nucleotides.

The fact that the third nucleotide from the 3'-end of the oligonucleotide is a 2'-O,4'-C-ethylene nucleotide (ENA) unit in (a) and (b) above means that the third nucleotide is not a natural nucleotide but an ENA nucleotide. It means, for example, that $A^{e2p}$ is used instead of $A^p$, $G^{e2p}$ is used instead of $G^p$, $5C^{e2p}$ or $C^{e2p}$ is used instead of $C^p$, and $T^{e2p}$ is used instead of $T^p$, for example.

Hereinafter, an oligonucleotide having the aforementioned characteristics is called a "Y-PRIMER."

(1)-2 Oligonucleotides used in detection of gene polymorphism in the present invention further include the following (c) and (d):

(c) an oligonucleotide, comprising a nucleotide sequence complementary to a reference sequence, except for the second nucleotide from the 3'-end thereof:
(i) wherein the 3'-end thereof is a nucleotide complementary to the reference nucleotide of a target gene;
(ii) wherein the second nucleotide from the 3'-end thereof (when the nucleotide at the 3'-end is defined as the first nucleotide) is a nucleotide that is not complementary to the nucleotide of a reference gene;
(iii) wherein the oligonucleotide has nucleotides complementary to the nucleotides of the target gene at the other positions;
(iv) wherein the third nucleotide from the 3'-end thereof (when the nucleotide at the 3'-end is defined as the first nucleotide) is a 2'-O,4'-C-ethylene nucleotide (ENA) unit, and the other nucleotides are natural nucleotides; and
(v) wherein the length of nucleotides thereof is not particularly limited, as long as it is able to amplify a nucleic acid in PCR, but the length is preferably 15 to 40 nucleotides, more preferably 18 to 35 nucleotides, and still more preferably 18 to 25 nucleotides.

Hereinafter, an oligonucleotide having the aforementioned characteristics is called an "N-PRIMER."

(d) an oligonucleotide, comprising a nucleotide sequence complementary to a mutant sequence except for the second nucleotide from the 3'-end thereof,
(i) wherein the 3'-end thereof is a nucleotide complementary to the mutant nucleotide of a target gene;
(ii) wherein the second nucleotide from the 3'-end thereof (when the nucleotide at the 3'-end is defined as the first nucleotide) is a nucleotide that is not complementary to the nucleotide of a reference gene;

(iii) wherein the oligonucleotide has nucleotides complementary to the nucleotides of the target gene at the other positions;

(iv) wherein the third nucleotide from the 3'-end thereof (when the nucleotide at the 3'-end is defined as the first nucleotide) is a 2'-O,4'-C-ethylene nucleotide (ENA) unit, and the other nucleotides are natural nucleotides; and (v) wherein the length of nucleotides thereof is not particularly limited, as long as it is able to amplify a nucleic acid in PCR, but the length is preferably 15 to 40 nucleotides, more preferably 18 to 35 nucleotides, and still more preferably 18 to 25 nucleotides.

Hereinafter, an oligonucleotide having the aforementioned characteristics is called a "P-PRIMER."

The fact that the third nucleotide from the 3'-end of the oligonucleotide is a 2'-O,4'-C-ethylene nucleotide (ENA) unit in (a) to (d) above means that the third nucleotide is not a natural nucleotide but an ENA nucleotide. It means that $A^{e2p}$ is used instead of $A^p$, $G^{e2p}$ is used instead of $G^p$, $5C^{e2p}$ or $C^{e2p}$ is used instead of $C^p$, and $T^{e2p}$ is used instead of $T^p$, for example.

These oligonucleotides described in (a) to (d) above may be referred to as forward primers.

(2) Oligonucleotides Used as a Pair (a) Oligonucleotides Used in PCR

The nucleotide sequence of an oligonucleotide used in PCR as a part of a pair with any oligonucleotide described in (a) to (d) in (1) above is not particularly limited, as long as it is able to amplify the sequence of interest in a gene used as a target in PCR, together with the oligonucleotide used in detection of gene polymorphism described in (a) to (d) in (1) above, in the nucleotide sequence of a gene used as a target for detection of gene polymorphism. Specifically, such a nucleotide sequence can be any given partial sequence consisting of 15 to 40, preferably 18 to 35, and more preferably 18 to 25 continuous nucleotides in a sequence which, rather than being at a position close to the 5'-end of the sequence of the strand which is complementary to the X primer, exists in a region towards the 5'-end of the strand. However, if an oligonucleotide used in detection of gene polymorphism and an oligonucleotide used therewith have sequences complementary to each other, they will anneal with each other, so that a non-specific sequence is amplified, thereby causing a risk of preventing detection of a specific gene polymorphism. Thus, it is preferable that the oligonucleotides be designed so as to avoid such a combination.

In the present specification, such an oligonucleotide used as part of a pair may be called a reverse primer.

(b) TaqMan Probe

The 5'-end of an oligonucleotide used in detection of gene polymorphism in TaqMan PCR (TaqMan probe) is labeled with a fluorescent reporter dye such as FAM or VIC, and the 3'-end thereof is labeled with a quencher [Genet. Anal., 14, pp. 143-149 (1999); J. Clin. Microbiol.], 34, pp. 2933-2936 (1996)].

The nucleotide sequence of the TaqMan probe used in a pair with any of the oligonucleotides described in (a) to (d) in (1) above is not particularly limited, as long as it is able to amplify the sequence of interest in a gene used as the target for detection of gene polymorphism in PCR, together with an oligonucleotide used in detection of gene polymorphism as described in (a) to (d) in (1) above. Specifically, such a nucleotide sequence can be any given partial sequence consisting of 15 to 40, preferably 18 to 35, and more preferably 18 to 25 continuous nucleotides in a sequence which, rather than being at a position close to the 5'-end of the sequence of the strand which is complementary to the X primer, exists in a region towards the 5'-end of the strand. However, if an oligonucleotide used in detection of gene polymorphism and the TaqMan probe have sequences complementary to each other, they will anneal to each other, so that a non-specific sequence is amplified, thereby causing a risk of preventing detection of a specific gene polymorphism. Thus, it is preferable that the above oligonucleotide and the TaqMan probe be designed, so as to avoid such a combination.

5. Method for Detecting Gene Polymorphism

A. Detection of Gene Polymorphism by PCR (1) PCR

The oligonucleotide used in detection of gene polymorphism, described in any one of (a) to (d) above, which was designed in the: "(1) Oligonucleotides used in detection of gene polymorphism" section, in the above chapter: "4. Oligonucleotide primer," and an oligonucleotide used as part of a pair with the above oligonucleotide, are used to perform a PCR reaction, so as to detect polymorphism at a certain position of a target gene. Herein, PCR can be carried out by any one of the following combinations: (i) the combination of an "X-PRIMER" with an oligonucleotide used in a pair with the aforementioned primer; (ii) the combination of a "Y-PRIMER" with an oligonucleotide used in a pair with the aforementioned primer; (iii) the combination of an "N-PRIMER" with an oligonucleotide used in a pair with the aforementioned primer; (iv) the combination of a "P-PRIMER" with an oligonucleotide used in a pair with the aforementioned primer; (v) the combination of (i) with (ii); and (vi) the combination of (iii) with (iv).

Reaction conditions for PCR are not particularly limited, as long as a desired nucleic acid sequence can be amplified under such conditions. Thus, PCR can be carried out under conditions which are generally applied by persons skilled in the art. For example, PCR can be carried out as follows.

(a) Nucleic Acid Synthesizing Enzyme

As a nucleic acid synthesizing enzyme, an enzyme can appropriately be selected from DNA polymerase, RNA polymerase and reverse transcriptase, depending on the type of nucleic acid used as a template. Examples of DNA polymerase used herein include Taq DNA polymerase derived from *Thermus aquaticus*, Tth DNA polymerase derived from *Thermus thermophilus*, KOD, Pfu, or Pwo DNA polymerase derived from *Pyrococcus*, and a mixture consisting of the aforementioned heat-resistant polymerases. However, examples are not limited thereto. Since Tth DNA polymerase also has RT activity, this enzyme is characterized in that it can be used alone when RT-PCR is carried out in a one tube-one step method. Reverse transcriptase means an enzyme capable of reverse transcribing RNA into cDNA. Examples of such reverse transcriptase include reverse transcriptases derived from bird Retroviruses such as Rous associated virus (RAV) or Avian myeloblastosis virus (AMV), reverse transcriptases derived from mouse retroviruses such as Moloney murine leukemia virus (MMLV), and the aforementioned Tth DNA polymerase. However, examples are not limited thereto.

(b) PCR Reaction

For example, a PCR reaction is carried out as follows:

Example of Reaction Solution Composition

Magnesium chloride 2 to 2.5 mM (preferably 2.5 mM);
1×PCR buffer (10 mM Tris-HCl (pH 8.3 to pH 9.0 at 25° C. (preferably pH 8.3)), 50 mM potassium chloride);
dNTPs 0.2 to 0.25 mM (preferably 0.25 mM);
The oligonucleotide used in detection of gene polymorphism and the oligonucleotide used in a pair with the above nucleotide 0.2 to 0.5 µM (preferably 0.2 µM); and Taq polymerase 1 to 2.5 units (preferably 2.5 units)

Sterilized water is added to the above solution, so as to adjust a total volume to 80 μl, and the total volume of the solution is then added to the total volume of the reaction solution obtained after completion of the reverse transcription reaction. Thereafter, PCR is initiated.

Reaction Temperature Conditions:

The reaction solution is first heated at 94° C. for 2 minutes. Thereafter, a temperature cycle consisting of: 90° C. to 95° C. (preferably 94° C.), 30 seconds; 40° C. to 65° C. (preferably, up to a temperature that is 20° C. lower than the dissociation temperature (Tm) calculated based on the properties of the primers), 30 seconds; and 70° C. to 75° C. (preferably 72° C.) for 1.5 minutes, is repeated for 28 to 50 cycles (preferably 30 cycles). Thereafter, the reaction solution is cooled to 4° C.

(2) Detection of Gene Polymorphism

After completion of PCR, the reaction solution is subjected to electrophoresis, so as to detect whether or not a band of the size of the sequence of interest has been amplified.

(a) Example Using an "X-PRIMER"

When amplification of a sequence of interest has been confirmed as a result of PCR with the combined use of an X-PRIMER with an oligonucleotide used in a pair with the aforementioned primer, it can be determined that the oligonucleotide in the polymorphic portion is complementary to the oligonucleotide at the 3'-end of X-PRIMER, and that there is no polymorphism.

On the other hand, when such a sequence of interest cannot be amplified, it can be determined that the oligonucleotide in the polymorphic portion is not complementary to the oligonucleotide at the 3'-end of X-PRIMER, and that there is polymorphism.

(b) Example Using a "Y-PRIMER"

When amplification of a sequence of interest can be confirmed as a result of PCR with the combined use of Y-PRIMER with an oligonucleotide used in a pair with the aforementioned primer, it can be determined that the oligonucleotide in the polymorphic portion is complementary to the oligonucleotide at the 3'-end of Y-PRIMER, and that there is polymorphism.

On the other hand, when such a sequence of interest cannot be amplified, it can be determined that the oligonucleotide in the polymorphic portion is not complementary to the oligonucleotide at the 3'-end of the Y-PRIMER, and that there is no polymorphism.

(c) Example Using Both an "X-PRIMER" and a "Y-PRIMER"

When amplification of a sequence of interest can be confirmed as a result of PCR with the combined use of an X-PRIMER with an oligonucleotide used in a pair with the aforementioned primer), but when such amplification of a sequence of interest cannot be confirmed as a result of PCR with the combined use of a Y-PRIMER with an oligonucleotide used in a pair with the aforementioned primer, it can be determined that there is no polymorphism.

On the other hand, when amplification of a sequence of interest cannot be confirmed as a result of PCR with the combined use of an X-PRIMER with an oligonucleotide used in a pair with the aforementioned primer, but when such amplification of a sequence of interest can be confirmed as a result of PCR with the combined use of a Y-PRIMER with an oligonucleotide used in a pair with the aforementioned primer, it can be determined that there is polymorphism.

(d) Example Using an "N-PRIMER"

When amplification of a sequence of interest can be confirmed as a result of PCR with the combined use of an N-PRIMER with an oligonucleotide used in a pair with the aforementioned primer, it can be determined that the oligonucleotide in the polymorphic portion is complementary to the oligonucleotide at the 3'-end of the N-PRIMER and that there is no polymorphism.

On the other hand, when such a sequence of interest cannot be amplified, it can be determined that the oligonucleotide in the polymorphic portion is not complementary to the oligonucleotide at the 3'-end of the "N-PRIMER" and that there is polymorphism.

(e) Example Using a "P-PRIMER"

When amplification of a sequence of interest can be confirmed as a result of PCR with the combined use of a P-PRIMER with an oligonucleotide used in a pair with the aforementioned primer, it can be determined that the oligonucleotide in the polymorphic portion is complementary to the oligonucleotide at the 3'-end of the P-PRIMER and that there is polymorphism.

On the other hand, when such a sequence of interest cannot be amplified, it can be determined that the oligonucleotide in the polymorphic portion is not complementary to the oligonucleotide at the 3'-end of the P-PRIMER and that there is no polymorphism.

(f) Example Using Both an "N-PRIMER" and a "P-PRIMER"

When amplification of a sequence of interest can be confirmed as a result of PCR with the combined use of an N-PRIMER with an oligonucleotide used in a pair with the aforementioned primer, but when such amplification of a sequence of interest cannot be confirmed as a result of PCR with the combined use of a P-PRIMER with an oligonucleotide used in a pair with the aforementioned primer, it can be determined that there is no polymorphism.

On the other hand, when amplification of a sequence of interest cannot be confirmed as a result of PCR with the combined use of an N-PRIMER with an oligonucleotide used in a pair with the aforementioned primer, but when such amplification of a sequence of interest can be confirmed as a result of PCR with the combined use of a P-PRIMER with an oligonucleotide used as a pair with the above primer, it can be determined that there is polymorphism.

When an experiment as described in any one of the aforementioned (a) to (f) is carried out using an oligonucleotide that does not contain an ENA oligonucleotide, it can be confirmed that a band appears due to non-complementary primer binding even in nucleic acid acting as a template which does not generally generate such a band. Thus, it can be confirmed that the present method enables detection of gene polymorphism at a higher sensitivity than that of the conventional method. In addition, even when LNA is used instead of the ENA unit, some non-complementary primer binding can be confirmed. Thus using LNA, the precision of detection of gene polymorphism is lower than with ENA.

Moreover, when an oligonucleotide is used in which the ENA unit is disposed at a position other than the third position from the 3'-end thereof, the precision and sensitivity of detection of gene polymorphism decrease.

B. Detection of Gene Polymorphism by TaqMan PCR

Using the oligonucleotide used in detection of gene polymorphism described in the above "A." section and the TaqMan probe described in the above "4." section, TaqMan PCR is carried out employing an ABI PRISM manufactured by ABI in accordance with protocols included therein, so as to detect gene polymorphism.

(a) Example Using an "X-PRIMER"

When amplification of a sequence of interest can be confirmed by an increase in fluorescence intensity as a result of PCR with the combined use of an X-PRIMER with the TaqMan probe, it can be determined that the oligonucleotide in the polymorphic portion is complementary to the oligonucleotide at the 3'-end of the X-PRIMER, and that there is no polymorphism.

On the other hand, when such a sequence of interest cannot be amplified, it can be determined that the oligonucleotide in the polymorphic portion is not complementary to the oligonucleotide at the 3'-end of the X-PRIMER, and that there is polymorphism.

(b) Example Using a "Y-PRIMER"

When amplification of a sequence of interest can be confirmed by an increase in fluorescence intensity as a result of PCR with the combined use of a Y-PRIMER with the TaqMan probe, it can be determined that the oligonucleotide in the polymorphic portion is complementary to the oligonucleotide at the 3'-end of the Y-PRIMER, and that there is polymorphism.

On the other hand, when such a sequence of interest cannot be amplified, it can be determined that the oligonucleotide in the polymorphic portion is not complementary to the oligonucleotide at the 3'-end of the Y-PRIMER, and that there is no polymorphism.

(c) Example Using Both an "X-PRIMER" and a "Y-PRIMER"

When amplification of a sequence of interest can be confirmed by an increase in fluorescence intensity as a result of PCR with the combined use of an X-PRIMER with the TaqMan probe, but when such amplification of a sequence of interest cannot be confirmed as a result of PCR with the combined use of a Y-PRIMER with the TaqMan probe, it can be determined that there is no polymorphism.

On the other hand, when amplification of a sequence of interest cannot be confirmed as a result of PCR with the combined use of an X-PRIMER with the TaqMan probe, but when such amplification of a sequence of interest can be confirmed by an increase in fluorescence intensity as a result of PCR with the combined use of a Y-PRIMER with the TaqMan probe, it can be determined that there is no polymorphism.

(d) Example Using an "N-PRIMER"

When amplification of a sequence of interest can be confirmed by an increase in fluorescence intensity as a result of PCR with the combined use of an N-PRIMER with the TaqMan probe, it can be determined that the oligonucleotide in the polymorphic portion is complementary to the oligonucleotide at the 3'-end of the N-PRIMER and that there is no polymorphism.

On the other hand, when such a sequence of interest cannot be amplified, it can be determined that the oligonucleotide in the polymorphic portion is not complementary to the oligonucleotide at the 3'-end of the N-PRIMER and that there is polymorphism.

(e) Example Using a "P-PRIMER"

When amplification of a sequence of interest can be confirmed by an increase in fluorescence intensity as a result of PCR with the combined use of a P-PRIMER with the TaqMan probe, it can be determined that the oligonucleotide in the polymorphic portion is complementary to the oligonucleotide at the 3'-end of the P-PRIMER and that there is polymorphism.

On the other hand, when such a sequence of interest cannot be amplified, it can be determined that the oligonucleotide in the polymorphic portion is not complementary to the oligonucleotide at the 3'-end of the P-PRIMER and that there is no polymorphism.

(f) Example Using Both an "N-PRIMER" and a "P-PRIMER"

When amplification of a sequence of interest can be confirmed by an increase in fluorescence intensity as a result of PCR with the combined use of an N-PRIMER with the TaqMan probe, but when such amplification of a sequence of interest cannot be confirmed as a result of PCR with the combined use of a P-PRIMER with the TaqMan probe, it can be determined that there is no polymorphism.

On the other hand, when amplification of a sequence of interest cannot be confirmed as a result of PCR with the combined use of an N-PRIMER with the TaqMan probe, but when such amplification of a sequence of interest can be confirmed by an increase in fluorescence intensity as a result of PCR with the combined use of a P-PRIMER with the TaqMan probe, it can be determined that there is no polymorphism.

C. Detection of Gene Polymorphism by a MALDI-TOF/MS Method

By partially modifying the method described in "A method for detecting polymorphism by MALDI-TOF/MS method", ("SNP *Idenshi Takei no Senryaku* (Strategy of SNP Gene Polymorphism)," (edited by Yusuke Nakamura), Nakayama Shoten, Tokyo, (2000), pp. 106-117), gene polymorphism can be detected. This method is specifically described below.

A PCR product containing a polymorphic portion is amplified from genomic DNA. In this reaction, bases corresponding to the polymorphic portion and PCR primers are designed such that they do not overlap with each other.

Subsequently, dNTP remaining in the PCR reaction system and an oligonucleotide used as a primer are eliminated, so as to obtain a purified PCR product.

The purified PCR product is used as a template. The oligonucleotide described in the section: "(1) Oligonucleotides used in detection of gene polymorphism" in the above chapter "4." is added to the above template in excess, such as 10 times or greater, and they are then annealed at a temperature between 90° C. and 95° C., followed by a thermal cycle reaction. The type of thermal cycle reaction is not particularly limited, as long as elongation of the oligonucleotide can be confirmed therein. For example, the reaction can be repeated 25 times between two temperatures, 94° C. and 37° C., so as to obtain a suitable elongation efficiency.

The elongation reaction product obtained is purified, so as to remove salts, buffer, surfactant, and protein. The purified product is spotted on a MALDI plate, and the mass thereof is then analyzed by MALDI-TOF/MS.

When the polymorphic portion of a target gene is an oligonucleotide that is complementary to an oligonucleotide used in detection of gene polymorphism, it is confirmed that an elongation reaction product that is formed by adding ddNTP to the oligonucleotide used in detection of gene polymorphism is amplified. However, when the polymorphic portion is not complementary to the oligonucleotide used in detection of gene polymorphism, such an elongation reaction product is not amplified.

If an elongation reaction product is confirmed when an X-PRIMER is used, it can be determined that the polymorphic portion is a reference nucleotide and that it does not have gene polymorphism. If such an elongation reaction product is not confirmed, it can be determined that the polymorphic portion is a mutant nucleotide and that it has gene polymorphism.

If an elongation reaction product is confirmed when a Y-PRIMER is used, it can be determined that the polymorphic portion is a mutant nucleotide and that it has gene polymorphism. If such an elongation reaction product is not confirmed, it can be determined that the polymorphic portion is a reference nucleotide and that it does not have gene polymorphism.

If an elongation reaction product is confirmed when an N-PRIMER is used, it can be determined that the polymorphic portion is a reference nucleotide and that it does not have gene polymorphism. If such an elongation reaction product is not confirmed, it can be determined that the polymorphic portion is a mutant nucleotide and that it has gene polymorphism.

If an elongation reaction product is confirmed when a P-PRIMER is used, it can be determined that the polymorphic portion is a mutant nucleotide and that it has gene polymorphism. If such an elongation reaction product is not confirmed, it can be determined that the polymorphic portion is a reference nucleotide and that it does not have gene polymorphism.

In addition, it is also possible to measure a PCR product by detecting the presence or absence of the generated PCR product, using the Quiagen LightCycler system and applying it to a kit for detecting such a PCR product (e.g. Quantitect SYBR Green PCR kit).

6. Confirmation of the Existence of Gene Polymorphism

The method of the present invention enables determination regarding whether polymorphism in nucleic acid used as a template is present in a hetero state or a homo state. Specifically, it can be determined by any one of the methods described in (a) to (f) below.

(a) Using an "X-PRIMER"

In the case where the amount of a band of interest seen is approximately half of that of an analyte which is known to be in a homo state, when amplification of a sequence of interest has been confirmed by PCR with the combined use of an X-PRIMER with an oligonucleotide used in a pair with the aforementioned primer, it can be determined that the polymorphism is in a hetero state consisting of a reference nucleotide and a mutant nucleotide.

(b) Example Using a Y-PRIMER

In the case where the amount of a band of interest seen is approximately half of that of an analyte which is known to be in a homo state, when amplification of a sequence of interest has been confirmed by PCR with the combined use of a Y-PRIMER with an oligonucleotide used in a pair with the aforementioned primer, it can be determined that the polymorphism is in a hetero state consisting of a reference nucleotide and a mutant nucleotide.

(c) Example Using Both an "X-PRIMER" and a "Y-PRIMER"

In the case where amplification of a sequence of interest can be confirmed as a result of PCR with the combined use of an X-PRIMER with an oligonucleotide used in a pair with the aforementioned primer, and where amplification of a sequence of interest can also be confirmed as a result of PCR with the combined use of a Y-PRIMER with an oligonucleotide used in a pair with the aforementioned primer, it can be determined that polymorphism is in a hetero state.

(d) Example Using an "N-PRIMER"

In the case where the amount of a band of interest seen is approximately half of that of an analyte which is known to be in a homo state, when amplification of a sequence of interest has been confirmed as a result of PCR with the combined use of an N-PRIMER with an oligonucleotide used in a pair with the aforementioned primer, it can be determined that polymorphism is in a hetero state consisting of a reference nucleotide and a mutant nucleotide.

(e) Example Using a "P-PRIMER"

In the case where the amount of a band of interest seen is approximately half of that of an analyte which is known to be in a homo state, when amplification of a sequence of interest has been confirmed as a result of PCR with the combined use of a P-PRIMER with an oligonucleotide used in a pair with the aforementioned primer, it can be determined that polymorphism is in a hetero state consisting of a reference nucleotide and a mutant nucleotide.

(f) Example Using Both an "N-PRIMER" and a "P-PRIMER"

In the case where amplification of a sequence of interest can be confirmed as a result of PCR with the combined use of an N-PRIMER with an oligonucleotide used in a pair with the aforementioned primer), and where amplification of a sequence of interest can also be confirmed as a result of PCR with the combined use of a P-PRIMER with an oligonucleotide used in a pair with the aforementioned primer, it can be determined that polymorphism is in a hetero state.

7. Kit for Detecting Gene Polymorphism

Primers and reagents used to carry out the methods of the present invention can be provided as a kit for detecting gene polymorphism. Such a kit may comprise the following items.

Kit 1:

(a) Oligonucleotide, wherein the third nucleotide from the 3'-end thereof is a 2'-O,4'-C-ethylene nucleotide (ENA) unit, the other nucleotides are natural nucleotides, the 3'-end nucleotide thereof is a nucleotide complementary to the reference nucleotide of a target gene, and at the other positions the nucleotides are complementary to the nucleotide sequence of the target gene;

(b) Oligonucleotide capable of amplifying a sequence of interest, together with the oligonucleotide described in (a) above;

(c) DNA polymerase; and
(d) PCR buffer.
  Kit 2:
A kit for detecting gene polymorphism comprising the following items:
(a) Oligonucleotide, wherein the third nucleotide from the 3'-end thereof is a 2'-O,4'-C-ethylene nucleotide (ENA) unit, the other nucleotides are natural nucleotides, the 3'-end nucleotide thereof is a nucleotide complementary to the mutant nucleotide of a target gene, and at the other positions the nucleotides are complementary to the nucleotide sequence of the target gene;
(b) Primer capable of amplifying a sequence of interest, together with the oligonucleotide described in (a) above;
(c) DNA polymerase; and
(d) PCR buffer.
  Kit 3:
(a) Oligonucleotide, wherein the third nucleotide from the 3'-end thereof is a 2'-O,4'-C-ethylene nucleotide (ENA) unit, the other nucleotides are natural nucleotides, the 3'-end nucleotide thereof is a nucleotide complementary to the reference nucleotide of a target gene, and at the other positions the nucleotides are complementary to the nucleotide sequence of the target gene;
(b) Oligonucleotide, wherein the third nucleotide from the 3'-end thereof is a 2'-O,4'-C-ethylene nucleotide (ENA) unit, the other nucleotides are natural nucleotides, the 3'-end nucleotide thereof is a nucleotide complementary to the mutant nucleotide of a target gene, and at the other positions the nucleotides are complementary to the nucleotide sequence of the target gene;
(c) Oligonucleotide capable of amplifying a sequence of interest, together with the oligonucleotide described in (a) or (b) above;
(d) DNA polymerase; and
(e) PCR buffer.
  Kit 4:
(a) Oligonucleotide,
(i) wherein the 3'-end nucleotide thereof is a nucleotide complementary to the reference nucleotide of a target gene;
(ii) wherein the second nucleotide from the 3'-end thereof (when the nucleotide at the 3'-end is defined as the first nucleotide) is a nucleotide that is not complementary to the nucleotide of a reference gene;
(iii) wherein the oligonucleotide has nucleotides complementary to the nucleotides of the target gene in the other positions;
(iv) wherein the third nucleotide from the 3'-end thereof (when the nucleotide at the 3'-end is defined as the first nucleotide) is a 2'-O,4'-C-ethylene nucleotide (ENA) unit, and the other nucleotides are natural nucleotides; and
(v) wherein the length of the oligonucleotide is not particularly limited, as long as it is able to amplify a nucleic acid in PCR, but such a length is preferably 15 to 40 nucleotides, more preferably 18 to 35 nucleotides, and still more preferably 18 to 25 nucleotides;
(b) Primer; capable of amplifying a sequence of interest, together with the oligonucleotide described in (a) above;
(c) DNA polymerase; and
(d) PCR buffer.
  Kit 5:
(a) Oligonucleotide,
(i) wherein the 3'-end nucleotide thereof is a nucleotide complementary to the mutant nucleotide of a target gene;
(ii) wherein the second nucleotide from the 3'-end thereof (when the nucleotide at the 3'-end is defined as the first nucleotide) is a nucleotide that is not complementary to the nucleotide of a reference gene;
(iii) wherein the oligonucleotide has nucleotides complementary to the nucleotides of the target gene in the other positions;
(iv) wherein the third nucleotide from the 3'-end thereof (when the nucleotide at the 3'-end is defined as the first nucleotide) is a 2'-O,4'-C-ethylene nucleotide (ENA) unit, and wherein the other nucleotides are natural nucleotides; and
(v) wherein the length of the oligonucleotide is not particularly limited, as long as it is able to amplify nucleic acid in PCR, but such a length is preferably 15 to 40 nucleotides, more preferably 18 to 35 nucleotides, and still more preferably 18 to 25 nucleotides;
(b) Primer capable of amplifying a sequence of interest, together with the oligonucleotide described in (a) above;
(c) DNA polymerase; and
(d) PCR buffer.

The kits 1 to 5 of the present invention may also comprise various types of reagents used in electrophoresis, dNTPs, a marker used in electrophoresis, etc., as necessary.

BRIEF DESCRIPTION OF THE DRAWINGS

FIG. 9-B is a view showing the results of PCR using KK mouse Nga strain-derived genomic DNA (KK/Nga) as a template.

BEST MODE FOR CARRYING OUT THE INVENTION

Figure 1:
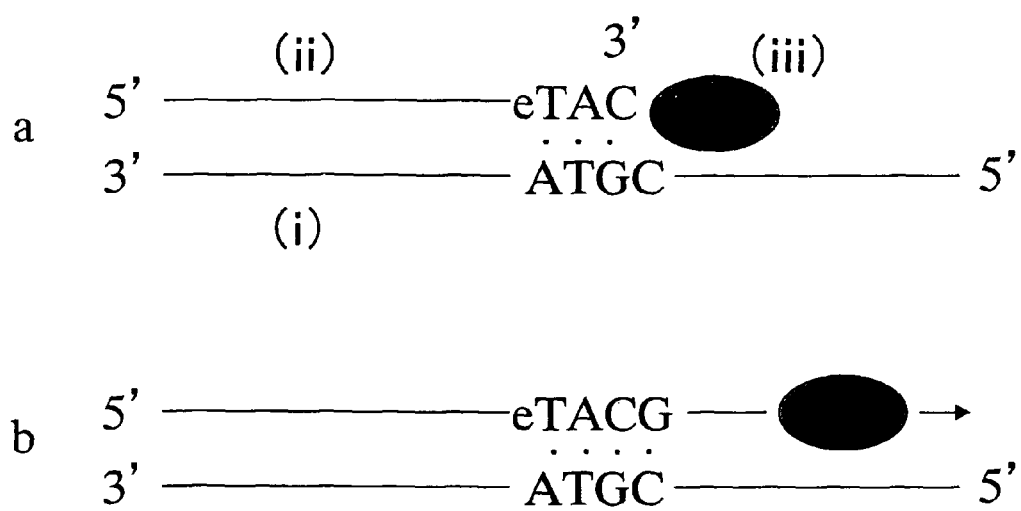
FIG. 1 is a view showing the principle of a method for detecting gene polymorphism when there is no polymorphism.
Figure 2:
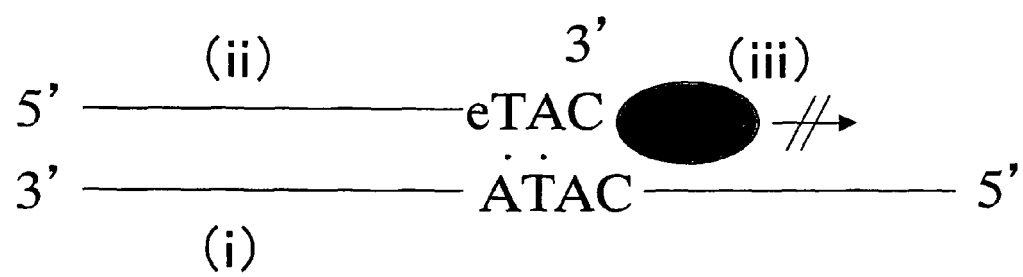
FIG. 2 is a view showing the principle of a method for detecting gene polymorphism when there is polymorphism.
Figure 3:
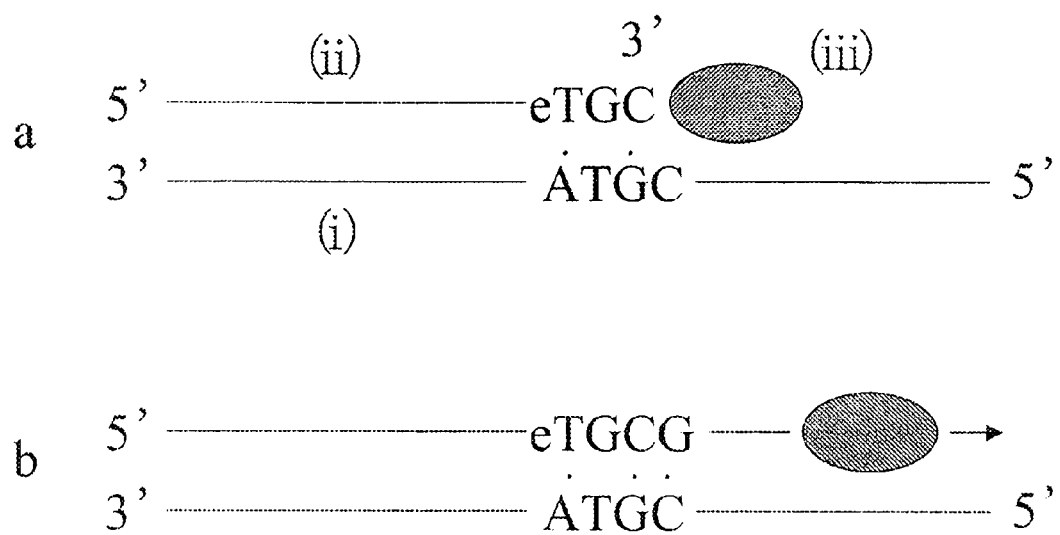
FIG. 3 is a view showing the principle of a method for detecting gene polymorphism when there is no polymorphism.
Figure 4:
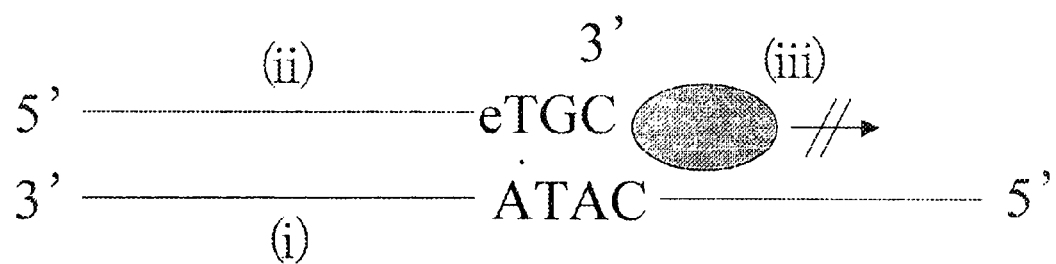
FIG. 4 is a view showing the principle of a method for detecting gene polymorphism when there is polymorphism.

The present invention will be more specifically described in the following examples, reference examples and test examples. However, these examples are not intended to limit the scope of the present invention. In the following examples, each genetic manipulation technique is carried out using a method described in Molecular Cloning, Sambrook, J., Fritsch, E. F. and Maniatis, T., Cold Spring Harbor Laboratory Press, 1989, or when commercially available reagents or kits are used, they are used in accordance with instructions included therewith, unless otherwise specified.

Example 1

Synthesis of HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^p$-$5C^{e2p}$-$T^p$-$C^t$ (SEQ ID NO: 11)

Using an automated nucleic acid synthesizer (ABI model 394 DNA/RNA synthesizer, manufactured by Perkin Elmer), the program was carried out at a scale of 40 nmol. With regard to the concentrations of a solvent, reagent and phosphoramidite in each synthesis cycle, the same concentrations as those for synthesis of a natural oligonucleotide were applied. Approximately 0.1 µmol of CPG was used. As a non-natural phosphoramidite, the compound described in Example 22 of Japanese Patent No. 3420984 (5'-O-dimethoxytrityl-2'-O,4'-C-ethylene 4-N-benzoyl-5-methylcytidine-3'-O-(2-cyanoethyl N,N-diisopropyl)phosphoramidite) was used. A protected oligonucleotide analogue having a sequence of interest was treated with concentrated ammonia water, so as to separate the oligomer from the support and to remove a cyanoethyl group as a protecting group on a phosphorus atom and a protecting group on a nucleobase. The solvent was evaporated under reduced pressure and the residue was purified by reverse phase HPLC (LC-10VP manufactured by Shimadzu Corporation, column: Merck, CHROMOLITH® Performance RP-18e (4.6×100 mm) (a HPLC column containing a single rod of high purity monolithic silica), solution A: 5% acetonitrile, 0.1 M triethylamine acetate aqueous solution (TEAA), pH 7.0; solution B: acetonitrile, B %: 10%→50% (10 min, linear gradient); 60° C.; 2 ml/min; 254 nm), so as to collect the peak of a product of interest having a dimethoxytrityl group. Thereafter, water was added thereto, and the mixture was then concentrated under reduced pressure, so as to remove TEAA. Thereafter, an 80% acetic acid aqueous solution (200 µl) was added and the mixture was then left for 20 minutes, to deprotect the dimethoxytrityl group. The solvent was distilled away, and the residue was purified by reverse phase HPLC (LC-10VP manufactured by Shimadzu Corporation, column: Merck, CHROMOLITH® Performance RP-18e (4.6×100 mm) (a HPLC column containing a single rod of high purity monolithic silica); solution A: 5% acetonitrile, 0.1 M TEAA, pH 7.0; solution B: 25% acetonitrile, 0.1 M TEAA, B %: 0%→40% (10 min, linear gradient); 60° C.; 2 ml/min; 254 nm), to collect the peak of a product of interest. The solvent was distilled away under reduced pressure and the residue was dissolved in 1 ml of water (9.4 $A_{260}$ units). In addition, the present compound was identified by negative-ion ESI mass spectrometry (calculated value: 6214.11, measurement value: 6214.62).

The nucleotide sequence of the present compound is complementary to a nucleotide sequence corresponding to nucleotide Nos. 26784-26803 of a human prothrombin gene (GenBank accession No. M17262).

Example 2

Synthesis of HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^p$-$5C^{e2p}$-$T^p$-$T^t$ (SEQ ID NO: 12)

The compound of Example 2 was synthesized in the same manner as described in Example 1 (21 $A_{260}$ units). The present compound was identified by negative-ion ESI mass spectrometry (calculated value: 6229.12, measurement value: 6229.21).

The nucleotide sequence of the present compound is complementary to a nucleotide sequence corresponding to nucleotide Nos. 26784-26803 of a human prothrombin gene (GenBank accession No. M17262), wherein G is mutated to A at nucleotide No. 26784.

Example 3

Synthesis of HO-$A^p$-$T^p$-$C^p$-$T^p$-$G^p$-$T^p$-$C^p$-$T^p$-$A^p$-$C^p$-$A^p$-$T^p$-$A^p$-$T^p$-$A^p$-$T^p$-$A^p$-$T^p$-$A^p$-$C^p$-$A^p$-$C^p$-$A^p$-$C^p$-$A^p$-$5C^{e2p}$-$A^p$-$T^t$ (SEQ ID NO: 13)

The compound of Example 3 was synthesized in the same manner as described in Example 1 (8.9 $A_{260}$ units). The present compound was identified by negative-ion ESI mass spectrometry (calculated value: 8530.67, measurement value: 8530.75).

The nucleotide sequence of the present compound corresponds to nucleotide Nos. 60529-60556 described in GenBank accession No. AL935325, wherein C is converted to T at nucleotide No. 60556.

Example 4

Synthesis of HO-$A^p$-$T^p$-$C^p$-$T^p$-$G^p$-$T^p$-$C^p$-$T^p$-$A^p$-$C^p$-$A^p$-$T^p$-$A^p$-$T^p$-$A^p$-$T^p$-$A^p$-$T^p$-$A^p$-$C^p$-$A^p$-$C^p$-$A^p$-$C^p$-$A^p$-$5C^{e2p}$-$A^p$$C^t$ (SEQ ID NO: 14)

The compound of Example 4 was synthesized in the same manner as described in Example 1 (10.1 $A_{260}$ units). The present compound was identified by negative-ion ESI mass spectrometry (calculated value: 8515.66, measurement value: 8515.56).

The nucleotide sequence of the present compound corresponds to nucleotide Nos. 60529-60556 described in GenBank accession No. AL935325.

Reference Example 1

HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^p$-$C^p$-$T^p$-$C^t$ (SEQ ID NO: 1)

The compound of Reference Example 1 was synthesized by a common method using an automated nucleic acid synthesizer.

The nucleotide sequence of the present compound is complementary to a nucleotide sequence corresponding to nucleotide Nos. 26784-26803 of a human prothrombin gene (GenBank accession No. M17262), and it is shown in SEQ ID NO: 1 of the sequence listing.

Reference Example 2

HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^p$-$C^p$-$T^p$-$T^t$ (SEQ ID NO: 2)

The compound of Reference Example 2 was synthesized by a common method using an automated nucleic acid synthesizer.

The nucleotide sequence of the present compound is complementary to a nucleotide sequence corresponding to nucleotide Nos. 26784-26803 of a human prothrombin gene (GenBank accession No. M17262), wherein G is mutated to A at nucleotide No. 26784. This sequence is shown in SEQ ID NO: 2 of the sequence listing.

Reference Example 3

Synthesis of HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^p$-$C^p$-$T^p$-$C^{e2t}$ (SEQ ID NO: 15)

The compound of Reference Example 3 was synthesized in the same manner as described in Example 1 (0.3 $A_{260}$ units). However, as non-natural phosphoramidite, the compound described in Example 5 of Japanese Patent No. 3420984 (5'-O-dimethoxytrityl-2'-O,4'-C-ethylene-4-N-benzoylcytidine-3'-O-(2-cyanoethyl N,N-diisopropyl)phosphoramidite) was used and as a solid support, approximately 0.1 μmol of universal-Q 500 CPG (manufactured by Glen Research) was used. The present compound was identified by negative-ion ESI mass spectrometry (calculated value: 6200.08, measurement value: 6200.25).

The nucleotide sequence of the present compound is complementary to a nucleotide sequence corresponding to nucleotide Nos. 26784-26803 of the human prothrombin gene (GenBank accession No. M17262).

Reference Example 4

Synthesis of HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^p$-$C^p$-$T^p$-$T^{e2t}$ (SEQ ID NO: 16)

The compound of Reference Example 4 was synthesized in the same manner as described in Example 1 (0.94 $A_{260}$ units). However, as non-natural phosphoramidite, the compound described in Example 9 of Japanese Patent No. 3420984 (5'-O-dimethoxytrityl-2'-O,4'-C-ethylene-5-methyluridine-3'-O-(2-cyanoethyl N,N-diisopropyl)phosphoramidite) was used and as a solid support, approximately 0.1 μmol of universal-Q 500 CPG (manufactured by Glen Research) was used. The present compound was identified by negative-ion ESI mass spectrometry (calculated value: 6215.09, measurement value: 6215.06).

The nucleotide sequence of the present compound is complementary to a nucleotide sequence corresponding to nucleotide Nos. 26784-26803 of the human prothrombin gene (GenBank accession No. M17262), wherein G is mutated to A at nucleotide No. 26784.

Reference Example 5

Synthesis of HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^p$-$C^p$-$T^{e2p}$-$C^t$ (SEQ ID NO: 17)

The compound of Reference Example 5 was synthesized in the same manner as described in Example 1 (2.28 $A_{260}$ units). However, as non-natural phosphoramidite, the compound described in Example 9 of Japanese Patent No. 3420984 (5'-O-dimethoxytrityl-2'-O,4'-C-ethylene-5-methyluridine-3'-O-(2-cyanoethyl N,N-diisopropyl)phosphoramidite) was used. The present compound was identified by negative-ion ESI mass spectrometry (calculated value: 6200.08, measurement value: 6200.26).

The nucleotide sequence of the present compound is complementary to a nucleotide sequence corresponding to nucleotide Nos. 26784-26803 of the human prothrombin gene (GenBank accession No. M17262).

Reference Example 6

Synthesis of HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$A^p$-$G^p$-$G^p$-$C^p$-$T^{e2p}$-$T^t$ (SEQ ID NO: 18)

The compound of Reference Example 6 was synthesized in the same manner as described in Example 1 (4.98 $A_{260}$ units). However, as non-natural phosphoramidite, the compound described in Example 9 of Japanese Patent No. 3420984 (5'-O-dimethoxytrityl-21-O,4'-C-ethylene-5-methyluridine-3'-O-(2-cyanoethyl N,N-diisopropyl)phosphoramidite) was used. The present compound was identified by negative-ion ESI mass spectrometry (calculated value: 6215.09, measurement value: 6215.26).

The nucleotide sequence of the present compound is complementary to a nucleotide sequence corresponding to nucleotide Nos. 26784-26803 of the human prothrombin gene (GenBank accession No. M17262), wherein G is mutated to A at nucleotide No. 26784.

Reference Example 7

Synthesis of HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^{e2p}$-$C^p$-$T^p$-$C^t$ (SEQ ID NO: 19)

The compound of Reference Example 7 was synthesized in the same manner as described in Example 1 (4.32 $A_{260}$ units). However, as non-natural phosphoramidite, the compound described in Example 27 of Japanese Patent No. 3420984 (5'-O-dimethoxytrityl-2'-O,4'-C-ethylene-2-N-isobutyrylguanosine-3'-O-(2-cyanoethyl N,N-diisopropyl)phosphoramidite) was used. The present compound was identified by negative-ion ESI mass spectrometry (calculated value: 6200.08, measurement value: 6199.95).

The nucleotide sequence of the present compound is complementary to a nucleotide sequence corresponding to nucleotide Nos. 26784-26803 of the human prothrombin gene (GenBank accession No. M17262).

Reference Example 8

Synthesis of HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^{e2p}$-$C^p$-$T^p$-$T^t$ (SEQ ID NO: 20)

The compound of Reference Example 8 was synthesized in the same manner as described in Example 1 (8.0 $A_{260}$ units). However, as non-natural phosphoramidite, the compound described in Example 27 of Japanese Patent No. 3420984 (5'-O-dimethoxytrityl-2'-O,4'-C-ethylene-2-N-isobutyrylguanosine-3'-O-(2-cyanoethyl N,N-diisopropyl)phosphoramidite) was used. The present compound was identified by negative-ion ESI mass spectrometry (calculated value: 6215.09, measurement value: 6215.06).

The nucleotide sequence of the present compound is complementary to a nucleotide sequence corresponding to nucleotide Nos. 26784-26803 of the human prothrombin gene (GenBank accession No. M17262), wherein G is mutated to A at nucleotide No. 26784.

Reference Example 9

Synthesis of HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^p$-$C^{e1p}$-$T^p$-$C^t$ (SEQ ID NO: 21)

The compound of Reference Example 9 was synthesized in the same manner as described in Example 1 (13.28 $A_{260}$ units). However, as non-natural phosphoramidite, the compound ($C^{e1p}$) 5'-O-dimethoxytrityl-2'-O,4'-C-methylene-4-N-benzoylcytidine-3'-O-(2-cyanoethyl N,N-diisopropyl)phosphoramidite, described in the publication, Tetrahedron (1998) 54, 3607-3630, was used. The present compound was identified by negative-ion ESI mass spectrometry (calculated value: 6186.05, measurement value: 6186.45).

The nucleotide sequence of the present compound is complementary to a nucleotide sequence corresponding to nucleotide Nos. 26784-26803 of the human prothrombin gene (GenBank accession No. M17262).

Reference Example 10

Synthesis of HO-$C^p$-$A^p$-$C^p$-$T^p$-$G^p$-$G^p$-$G^p$-$A^p$-$G^p$-$C^p$-$A^p$-$T^p$-$T^p$-$G^p$-$A^p$-$G^p$-$G^p$$C^{e1p}$-$T^p$-$T^t$ (SEQ ID NO: 22)

The compound of Reference Example 10 was synthesized in the same manner as described in Example 1 (8.0 $A_{260}$ units). However, as non-natural phosphoramidite, the compound ($C^{e2p}$), 5'-O-dimethoxytrityl-2'-O,4'-C-methylene-4-N-benzoylcytidine-3'-O-(2-cyanoethyl N,N-diisopropyl)phosphoramidite, described in the publication, Tetrahedron (1998) 54, 3607-3630, was used. The present compound was identified by negative-ion ESI mass spectrometry (calculated value: 6201.07, measurement value: 6201.14).

The nucleotide sequence of the present compound is complementary to a nucleotide sequence corresponding to nucleotide Nos. 26784-26803 of the human prothrombin gene (GenBank accession No. M17262), wherein G is mutated to A at nucleotide No. 26784.

Reference Example 11

Synthesis of HO-$A^p$-$T^p$-$C^p$-$T^p$-$G^p$-$T^p$-$C^p$-$T^p$-$A^p$-$C^p$-$A^p$-$T^p$-$A^p$-$T^p$-$A^p$-$T^p$-$A^p$-$T^p$-$A^p$-$C^p$-$A^p$-$C^p$-$A^p$-$C^p$-$A^p$-$C^p$-$A^p$-$T^t$ (SEQ ID NO: 3)

The compound of Reference Example 11 was synthesized by a common method using an automated nucleic acid synthesizer.

The nucleotide sequence of the present compound corresponds to nucleotide Nos. 60529-60556 described in GenBank accession No. AL935325, wherein C is converted to T at nucleotide No. 60556. This sequence is shown in SEQ ID NO: 3 of the sequence listing.

Reference Example 12

Synthesis of HO-$A^p$-$T^p$-$C^p$-$T^p$-$G^p$-$T^p$-$C^p$-$T^p$-$A^p$-$C^p$-$A^p$-$T^p$-$A^p$-$T^p$-$A^p$-$T^p$-$A^p$-$T^p$-$A^p$-$C^p$-$A^p$-$C^p$-$A^p$-$C^p$-$A^p$-$C^t$ (SEQ ID NO: 4)

The compound of Reference Example 12 was synthesized by a common method using an automated nucleic acid synthesizer.

The nucleotide sequence of the present compound corresponds to nucleotide Nos. 60529-60556 described in GenBank accession No. AL935325. This sequence is shown in SEQ ID NO: 4 of the sequence listing.

Reference Example 13

Synthesis of HO-$A^p$-$T^p$-$C^p$-$T^p$-$G^p$-$T^p$-$C^p$-$T^p$-$A^p$-$C^p$-$A^p$-$T^p$-$A^p$-$T^p$-$A^p$-$T^p$-$A^p$-$T^p$-$A^p$-$C^p$-$A^p$-$C^p$-$A^p$-$C^p$-$A^p$-$C^p$-$A^p$-$T^{e2t}$ (SEQ ID NO: 23)

The compound of Reference Example 13 was synthesized in However, as non-natural phosphoramidite, the compound described in Example 9 of Japanese Patent No. 3420984 (5'-O-dimethoxytrityl-2'-O,4'-C-ethylene-5-methyluridine-3'-O-(2-cyanoethyl N,N-diisopropyl)phosphoramidite) was used, and as a solid support, approximately 0.1 µmol of universal-Q 500 CPG (manufactured by Glen Research) was used. The present compound was identified by negative-ion ESI mass spectrometry (calculated value: 8516.64, measurement value: 8515.88).

The nucleotide sequence of the present compound corresponds to nucleotide Nos. 60529-60556 described in GenBank accession No. AL935325, wherein C is converted to T at nucleotide No. 60556.

Reference Example 14

Synthesis of HO-$A^p$-$T^p$-$C^p$-$T^p$-$G^p$-$T^p$-$C^p$-$T^p$-$A^p$-$C^p$-$A^p$-$T^p$-$A^p$-$T^p$-$A^p$-$T^p$-$A^p$-$T^p$-$A^p$-$C^p$-$A^p$-$C^p$-$A^p$-$C^p$-$A^p$-$C^p$-$A^p$-$5C^{e2t}$ (SEQ ID NO: 24)

The compound of Reference Example 14 was synthesized in the same manner as described in Example 1 (7.4 $A_{260}$ units). However, as a solid phase carrier, approximately 0.1 µmol of universal-Q 500 CPG (manufactured by Glen Research) was used. The present compound was identified by negative-ion ESI mass spectrometry (calculated value: 8516.66, measurement value: 8516.00).

The nucleotide sequence of the present compound corresponds to nucleotide Nos. 60529-60556 described in GenBank accession No. AL935325.

Reference Example 15

Synthesis of HO-$A^p$-$T^p$-$C^p$-$T^p$-$G^p$-$T^p$-$C^p$-$T^p$-$A^p$-$C^p$-$A^p$-$T^p$-$A^p$-$T^p$-$A^p$-$T^p$-$A^p$-$T^p$-$A^p$-$C^p$-$A^p$-$C^p$-$A^p$-$C^p$-$A^p$-$C^p$-$A^p$-$C^p$-$A^{e2p}$-$T^t$ (SEQ ID NO: 25)

The compound of Reference Example 15 was synthesized in the same manner as described in Example 1 (8.4 $A_{260}$ units). However, as non-natural phosphoramidite, the compound described in Example 14 of Japanese Patent No. 3420984 (5'-O-dimethoxytrityl-2'-O,4'-C-ethylene-6-N-benzoyladenosine-3'-O-(2-cyanoethyl N,N-diisopropyl)phosphoramidite) was used. The present compound was identified by negative-ion ESI mass spectrometry (calculated value: 8516.64, measurement value: 8516.32).

The nucleotide sequence of the present compound corresponds to nucleotide Nos. 60529-60556 described in GenBank accession No. AL935325, wherein C is converted to T at nucleotide No. 60556.

Reference Example 16

Synthesis of HO-$A^p$-$T^p$-$C^p$-$T^p$-$G^p$-$T^p$-$C^p$-$T^p$-$A^p$-$C^p$-$A^p$-$T^p$-$A^p$-$T^p$-$A^p$-$T^p$-$A^p$-$T^p$-$A^p$-$C^p$-$A^p$-$C^p$-$A^p$-$C^p$-$A^p$-$C^p$-$A^{e2p}$-$C^t$ (SEQ ID NO: 26)

The compound of Reference Example 16 was synthesized in the same manner as described in Example 1 (7.9 $A_{260}$ units). However, as non-natural phosphoramidite, the compound described in Example 14 of Japanese Patent No. 3420984 (5'-O-dimethoxytrityl-2'-O,4'-C-ethylene-6-N-benzoyladenosine-3'-O-(2-cyanoethyl N,N-diisopropyl)phosphoramidite) was used. The present compound was identified by negative-ion ESI mass spectrometry (calculated value: 8501.63, measurement value: 8500.70).

The nucleotide sequence of the present compound corresponds to nucleotide Nos. 60529-60556 described in GenBank accession No. AL935325.

Reference Example 17

Synthesis of HO-$A^p$-$T^p$-$C^p$-$T^p$-$G^p$-$T^p$-$C^p$-$T^p$-$A^p$-$C^p$-$A^p$-$T^p$-$A^p$-$T^p$-$A^p$-$T^p$-$A^p$-$T^p$-$A^p$-$C^p$-$A^p$-$C^p$-$A^p$-$C^p$-$A^{e2p}$-$C^p$-$A^p$-$T^t$ (SEQ ID NO: 27)

The compound of Reference Example 17 was synthesized in the same manner as described in Example 1 (9.7 $A_{260}$ units). However, as non-natural phosphoramidite, the compound described in Example 14 of Japanese Patent No. 3420984 (5'-O-dimethoxytrityl-2'-O,4'-C-ethylene-6-N-benzoyladenosine-3'-O-(2-cyanoethyl N,N-diisopropyl)phosphoramidite) was used. The present compound was identified by negative-ion ESI mass spectrometry (calculated value: 8516.64, measurement value: 8517.14).

The nucleotide sequence of the present compound corresponds to nucleotide Nos. 60529-60556 described in GenBank accession No. AL935325, wherein C is converted to T at nucleotide No. 60556.

Reference Example 18

Synthesis of HO-$A^p$-$T^p$-$C^p$-$T^p$-$G^p$-$T^p$-$C^p$-$T^p$-$A^p$-$C^p$-$A^p$-$T^p$-$A^p$-$T^p$-$A^p$-$T^p$-$A^p$-$T^p$-$A^p$-$C^p$-$A^p$-$C^p$-$A^p$-$C^p$-$A^{e2p}$-$C^p$-$A^p$-$C^t$ (SEQ ID NO: 28)

The compound of Reference Example 18 was synthesized in the same manner as described in Example 1 (7.2 $A_{260}$ units). However, as non-natural phosphoramidite, the compound described in Example 14 of Japanese Patent No. 3420984 (5'-O-dimethoxytrityl-2'-O,4'-C-ethylene-6-N-benzoyladenosine-3'-O-(2-cyanoethyl N,N-diisopropyl)phosphoramidite) was used. The present compound was identified by negative-ion ESI mass spectrometry (calculated value: 8501.63, measurement value: 8501.65).

The nucleotide sequence of the present compound corresponds to nucleotide Nos. 60529-60556 described in GenBank accession No. AL935325.

Test Example 1

Detection of SNP in Human Prothrombin Gene

In order to detect SNP (F2 20210G-A) in a human prothrombin gene (coagulation factor II; GenBank accession No. M17262), a reverse primer and human DNA were prepared using TrueSNP Demo Kit (Proligo) in accordance with the protocols included therein. The nucleotide sequence of the reverse primer corresponds to nucleotide Nos. 26588-26605 of GenBank accession No. M17262. The sequence is as follows:

```
5'-GGGTGAAGGCTGTGACCG-3'
(SEQ ID NO: 5 of the sequence listing)
```

As a forward primer, the compound (1.25 μM) described in any one of Examples 1 and 2, and Reference Examples 1 to 8, was used. A solution comprising 5 μl of the forward primer, 1.3 μl of the reverse primer, 12.5 μl of Premix Taq (manufactured by Takara Shuzo Co., Ltd.), 1 μl of a human DNA solution, and 5.2 μl of sterilized water, was subjected to a PCR reaction (Hot Start method), using a Takara PCR Thermal Cycler PERSONAL (TP240). As the reaction cycle, after a treatment at 94° C. for 10 minutes, a cycle consisting of 94° C., 1 minute, 63° C., 1 minute, and 72° C., 1 minute, was repeated for 31 cycles. After completion of the reaction, 1 μl of a loading solution was added to 5 μl of the reaction solution, this was followed by 10% polyacrylamide gel electrophoresis (1×TBE, 200 V constant voltage, approximately 1 hour). Thereafter, the resultant gel was stained with SYBR Green I (manufactured by Cambrex), and the Molecular Imager FX Fluorescent Imager system (Bio-Rad) was used to visualize the band. Thereafter, it was quantified using Quantity One software (Bio-Rad).

Figure 5:
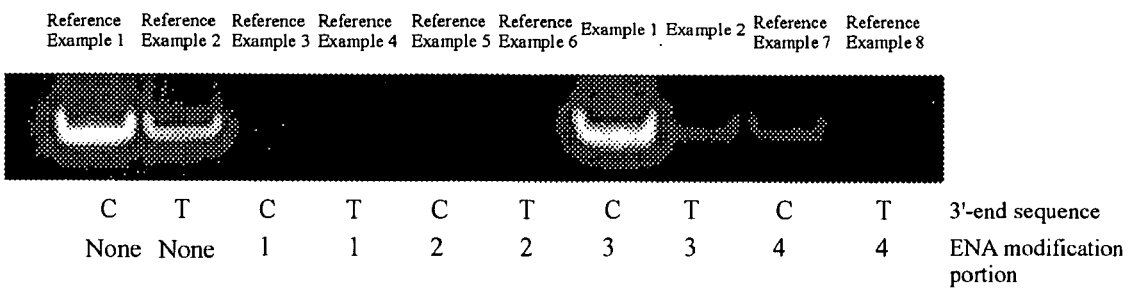
FIG. 5 is a view showing the results of PCR using Premix Taq and various types of primers.

The results are shown in FIG. 5. When a compound, wherein an ENA unit had been introduced into the third position from the 3'-end thereof, was used as a forward primer, in the case of the compound of Example 1, amplification of the gene of interest (216 bp) could be confirmed, but in the case of the compound of Example 2, amplification of the gene of interest (216 bp) could not be confirmed. In contrast, when the compounds of Reference Examples 1 and 2, which were natural oligonucleotides, were used as forward primers, not only in the case of the compound of Reference Example 1, but also in the case of the compound of Reference Example 2, amplification of the gene of interest was confirmed, and thus amplification of the gene due to non-complementary binding took place. On the other hand, in the case of the compounds of Reference Examples 3 and 4, wherein an ENA unit had been introduced into the 3'-end thereof, and in the case of the compounds of Reference Examples 5 and 6, wherein such an ENA unit had been introduced into the second position from the 3'-end thereof, amplification of a gene of interest was not confirmed. These results revealed that when a compound, wherein an ENA unit has been introduced into the third position from the 3'-end thereof is used as a primer, there is almost no non-complementary binding, thereby selectively amplifying the gene (216 bp).

Figure 6:
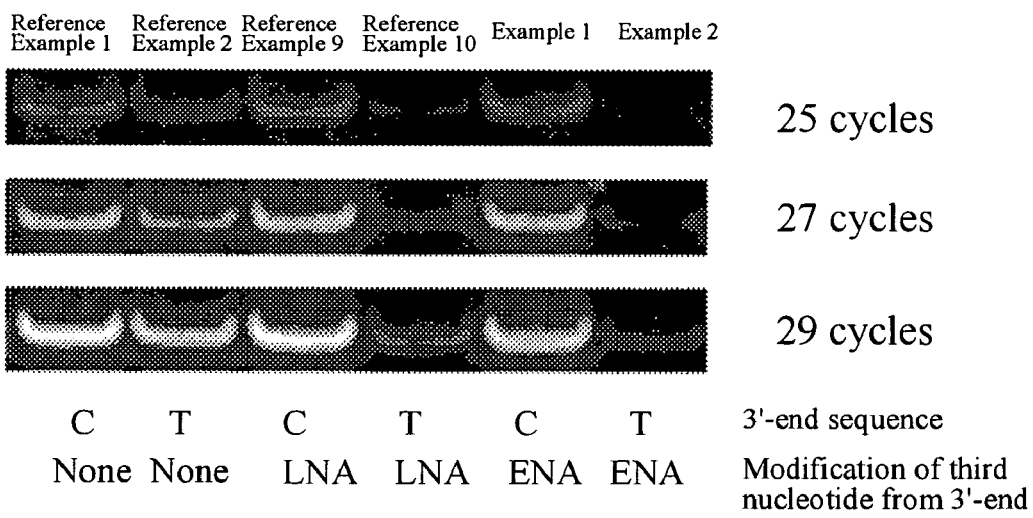
FIG. 6 is a view showing the results of PCR using Premix EX Taq and various types of primers.

FIG. 6 shows an example using Premix EX Taq (manufactured by Takara Shuzo Co., Ltd.) instead of Premix Taq (manufactured by Takara Shuzo Co., Ltd.). In this case also, when a primer wherein an ENA unit had been introduced into the third position from the 3'-end thereof was used, almost no non-complementary binding took place, and when the primer of Example 1 was used, the gene was amplified more efficiently and selectively.

Figures 7, 8:
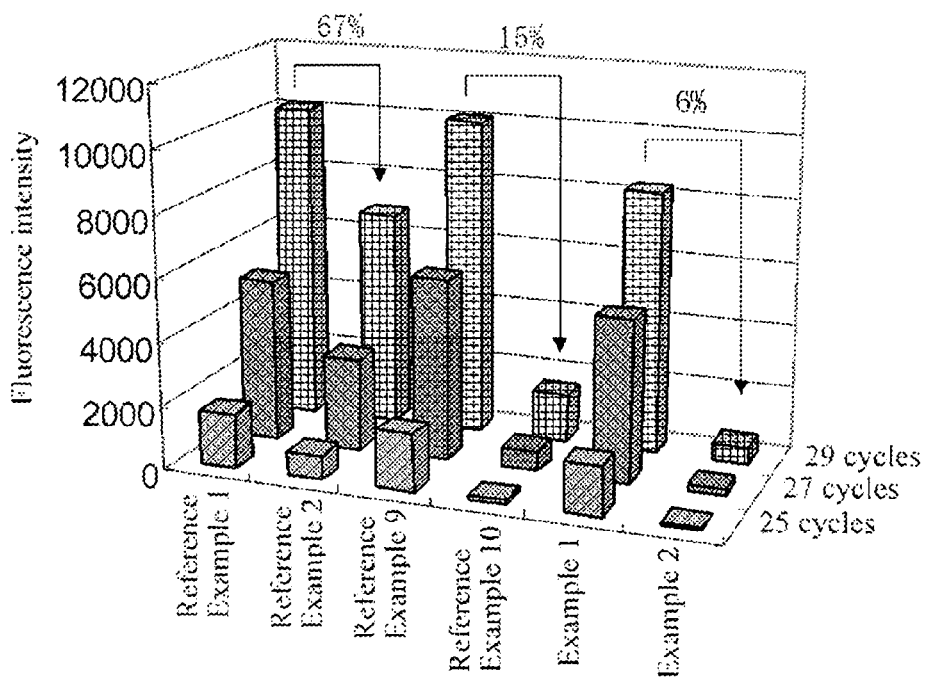
FIG. 7 is a view showing the fluorescence intensity of each band detected by PCR, which has been converted into numerical values.
FIG. 8 is a view showing polymorphism in an angiopoietin-like 3 gene promoter.

The fluorescence intensity of the detected band was converted into a numerical value, and it was then plotted, as shown in FIG. 7. In the case of the compounds of Reference Examples 9 and 10, an LNA unit was introduced into the third position from the 3'-end thereof. When the compound of Reference Example 10 was used as the forward primer, 15% amplification of the gene due to non-complementary binding was observed. In contrast, when the compound of Example 2, wherein an ENA unit had been introduced into the third position from the 3'-end thereof, was used as a forward primer, only 6% amplification of the gene due to non-complementary binding was observed. Thus, it was revealed that such an ENA unit results in little non-complementary binding, having high selectivity.

Test Example 2

Detection of Polymorphism in Angiopoietin-Like 3 Gene Promoter (1) Preparation of Mouse Genomic DNA A tail tip (1.5 cm) collected from each of the mice (mouse AKR strain, KK mouse Nga strain, and KK mouse Snk strain (4-week-old)) was immersed in 840 μl of a dissolving solution (consisting of 720 μl of 1×SSC, 80 μl of 10% SDS, and 40 μl of 10 mg/ml proteinase K) and the samples were then shaken overnight while being incubated at 50° C. Subsequently, 20 μl of 1 mg/ml ribonuclease A was added to the reaction solution, and it was then incubated at 50° C. for 1 hour. Thereafter, phenol-chloroform extraction was carried out twice, and an ethanol precipitation operation was then carried out once. The precipitate was dissolved in 150 μl of a buffer comprising 10 mM Tris-HCl (pH 7.5) and 1 mM EDTA. Thereafter, the solution was subjected to spectrophotometry (U-3000, manufactured by Hitachi, Ltd.), so as to measure the absorbance at a wavelength of 260 nm. Thereafter, sterilized water was added thereto so as to adjust the concentration to 25 ng/μl, thereby preparing a genomic DNA sample.

(2) PCR

From the results of direct sequencing, polymorphism in the angiopoietin-like protein 3 gene promoter is as shown in FIG. 8. FIG. 8 shows that when compared with the mouse KK/Nga strain and the KK/Snk strain, the mouse AKR strain has polymorphism, such that 2 bases (CA) indicated with the mark ":" are deleted.

As the reverse primer for PCR, a primer having the following sequence was used:

```
5'-GTCACTAGACTACTGCTTACTGTCC-3'
(SEQ ID NO: 6 of the sequence listing)
```

The nucleotide sequence of the present compound is complementary to a sequence corresponding to nucleotide Nos. 60658-60682 described in GenBank accession No. AL935325. As the forward primer, a compound (1.25 mM) described in any of Examples 3 and 4 and Reference Examples 11 to 18 was used. A solution comprising 5 ml (1.25 mM) of the forward primer, 5 ml (1.25 mM) of the reverse primer, 12.5 ml of Premix Taq (manufactured by Takara Shuzo Co., Ltd.), 0.125 ml of the genomic DNA solution (100 ng/1 ml) and 2.38 ml of sterilized water was subjected to a PCR reaction (Hot Start method), using a Takara PCR Thermal Cycler PERSONAL (TP240). As the reaction cycle, after a heat treatment at 94° C. for 10 minutes, a cycle consisting of 94° C., 1 minute, 63° C., 1 minute, and 72° C., 1 minute, was repeated for 30 cycles. After completion of the reaction, 1 ml of a loading solution was added to 5 ml of the reaction solution, this was followed by 10% polyacrylamide gel electrophoresis (1×TBE, 200 V constant voltage, approximately 1 hour). Thereafter, the resultant gel was stained with SYBR Green I (manufactured by Cambrex), and the Molecular Imager FX Fluorescent Imager system (Bio-Rad) was used to visualize the band.

(3) Results

Figure 9:
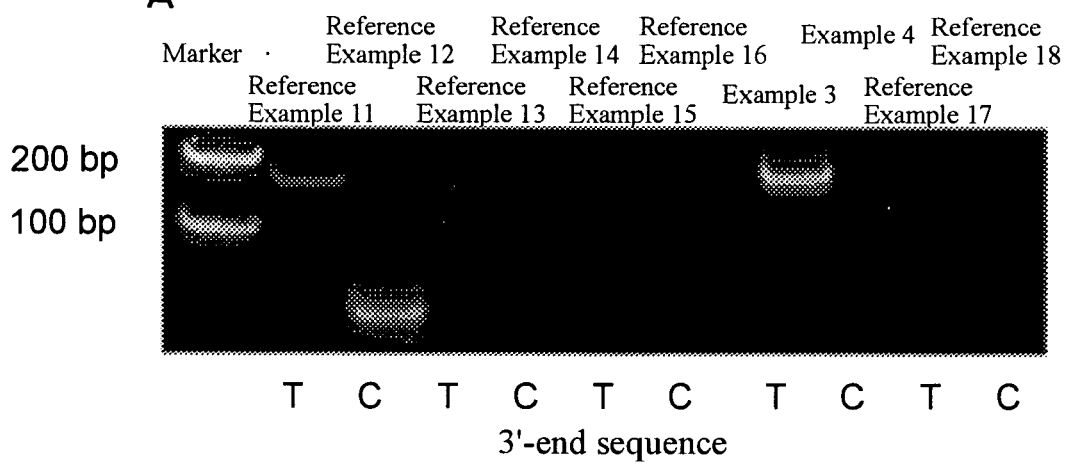
FIG. 9-A is a view showing the results of PCR using mouse AKR strain-derived genomic DNA (AKR) as a template.
Figure 9:
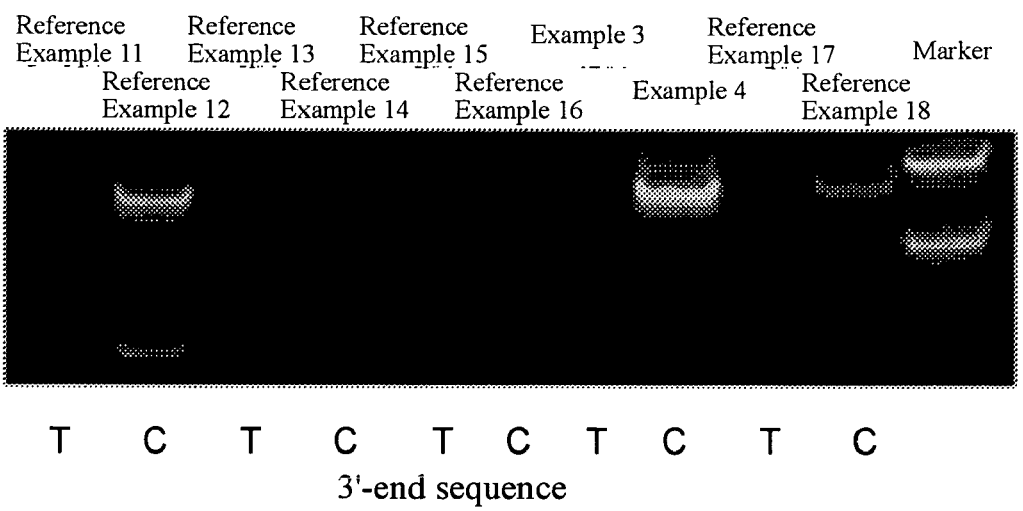

The results obtained using the mouse AKR strain-derived genomic DNA (AKR) as the template are shown in FIG. 9-A. It was found that in the compounds of Examples 3 and 4, wherein an ENA unit has been introduced into the third position from the 3'-end thereof, in the case of using the compound of Example 3 as a forward primer, a gene (152 bp) was selectively amplified.

The results obtained using the KK mouse Nga strain-derived genomic DNA (KK/Nga) as the template are shown in FIG. 9-B. It was found that in the compounds of Examples 3 and 4, wherein an ENA unit has been introduced into the third position from the 3'-end thereof, in the case of using the compound of Example 4 as the forward primer, the gene (154 bp) was amplified most efficiently and selectively.

Figure 10:
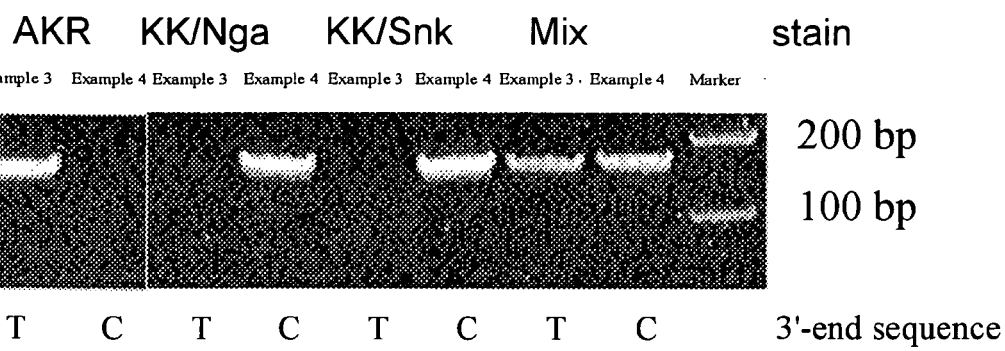
FIG. 10 is a view showing the results of PCR, using, as templates, AKR genomic DNA, KK/Nga genomic DNA, KK mouse Snk strain (KK/Snk) genomic DNA, and DNA formed by mixing equal amounts of AKR and KK/Nga genomic DNAs.

FIG. 10 shows the results of PCR, using the compounds of Example 3 and 4 as forward primers and also using, as a template, AKR genomic DNA, KK/Nga genomic DNA, KK mouse Snk strain (KK/Snk) genomic DNA and DNA (Mix) formed by mixing equal amounts of AKR and KK/Nga genomic DNAs. As shown in FIG. 10A, in the case of AKR, when the compound of Example 3 was used as the forward primer, selective amplification of the gene was confirmed. In the case of KK/Nga and KK/Snk, when the compound of Example 4 was used as the forward primer, selective amplification of the gene was confirmed. In the case of Mix, in both cases of using the compound of Example 3 or the compound of Example 4 as the forward primer, amplification of the gene was confirmed. Thus, it was indicated that even if polymorphism is in a hetero state, it is distinguishable. Moreover, as shown in FIG. 10B, when the compounds of Reference Examples 11 and 12, which are natural DNA primers, were used as forward primers, by-products were observed in addition to amplification of the band of interest. Thus, it was found that the combination of the compound of Example 3 with that of Example 4, wherein an ENA unit has been introduced into the third position from the 3'-end thereof, is far better in terms of detection of gene polymorphism.

Example 5

Synthesis of HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^{e2p}$-$T^p$-$G^t$ (SEQ ID NO: 29)

Using an automated nucleic acid synthesizer (ABI model 394 DNA/RNA synthesizer, manufactured by Perkin Elmer), the program was carried out at a scale of 40 nmol, so as to synthesize HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^{e2p}$-$T^p$-$G^t$ (SEQ ID NO: 29) (hereinafter referred to as "primer A"). With regard to the concentrations of solvent, reagent and phosphoramidite in each synthesis cycle, the same concentrations as used for the synthesis of the natural oligonucleotide were applied. Approximately 0.1 μmol of CPG was used. As non-natural phosphoramidite, the compound described in Example 27 of Japanese Patent No. 3420984 (5'-O-dimethoxytrityl-2'-O,4'-C-ethylene-2-N-isobutyrylguanosine-3'-O-(2-cyanoethyl N,N-diisopropyl)phosphoramidite) was used. A protected oligonucleotide analogue having a sequence of interest was treated with concentrated ammonia water, so as to separate the oligomer from the support and so as also to remove the cyanoethyl group as protecting group on the phosphorus atom and the protecting group on the nucleobase. The solvent was distilled away under reduced pressure and the residue was purified by reverse phase HPLC (LC-10VP manufactured by Shimadzu Corporation, column: Merck, CHROMOLITH®

Performance RP-18e (4.6×100 mm)(a HPLC column containing a single rod of high purity monolithic silica), solution A: 5% acetonitrile, 0.1 M triethylamine acetate aqueous solution (TEAA), pH 7.0, solution B: acetonitrile, B %: 10%→50% (10 min, linear gradient); 60° C.; 2 ml/min; 254 nm), so as to collect the peak with the product of interest having a dimethoxytrityl group. Thereafter, water was added thereto, and the mixture was then concentrated under reduced pressure, so as to remove TEAA. Thereafter, an 80% acetic acid aqueous solution (200 μl) was added thereto, and the mixture was then left for 20 minutes, so as to deprotect the dimethoxytrityl group. The solvent was evaporated, and the residue was purified by reverse phase HPLC (LC-10VP manufactured by Shimadzu Corporation, column: Merck, CHROMOLITH® Performance RP-18e (4.6×100 mm) (a HPLC column containing a single rod of high purity monolithic silica), solution A: 5% acetonitrile, 0.1 M TEAA, pH 7.0, solution B: 25% acetonitrile, 0.1 M TEAA, B %: 0%→40% (10 min, linear gradient); 60° C.; 2 ml/min; 254 nm), so as to collect the peak with the product of interest. The solvent was distilled away under reduced pressure and the residue was dissolved in 1 ml of water. The present compound was identified by MALDI-TOF mass spectrometry (calculated value: 7625.0, measurement value: 7624.1).

The nucleotide sequence of the present compound (primer A) is complementary to a nucleotide sequence corresponding to nucleotide Nos. 60499-60523 described in GenBank accession No. AL935325.14, wherein C is converted to T at nucleotide No. 60522 and wherein A is converted to G at nucleotide No. 60523.

Example 6

Synthesis of HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^{e2p}$-$T^p$-$A^t$
(SEQ ID NO: 30)

HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^{e2p}$ $T^p$-$A^t$ (SEQ ID NO: 30) (hereinafter referred to as "primer B") was synthesized by the same method as that of Example 5, and the compound was then identified by MALDI-TOF mass spectrometry (calculated value: 7609.0, measurement value: 7609.2).

The nucleotide sequence of the present compound (primer B) is a sequence corresponding to nucleotide Nos. 60499-60523 described in GenBank accession No. AL935325.14, wherein C is converted to T at nucleotide No. 60522.

Example 7

Synthesis of HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^{e2p}$-$G^p$-$G^t$
(SEQ ID NO: 31)

HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$$G^{e2p}$-$G^p$-$G^t$ (SEQ ID NO: 31) (hereinafter referred to as "primer C") was synthesized by the same method as that of Example 1 and the compound was then identified by MALDI-TOF mass spectrometry (calculated value: 7650.0, measurement value: 7649.4).

The nucleotide sequence of the present compound (primer C) is a sequence corresponding to nucleotide Nos. 60499-60523 described in GenBank accession No. AL935325.14, wherein C is converted to G at nucleotide No. 60522 and wherein A is converted to G at nucleotide No. 60523.

Example 8

Synthesis of HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^{e2p}$-$G^p$-$A^t$
(SEQ ID NO: 32)

HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^{e2p}$-$G^p$$A^t$ (SEQ ID NO: 32) (hereinafter referred to as "primer D") was synthesized by the same method as that of Example 5, and the compound was then identified by MALDI-TOF mass spectrometry (calculated value: 7634.1, measurement value: 7634.2).

The nucleotide sequence of the present compound (primer D) is a sequence corresponding to nucleotide Nos. 60499-60523 described in GenBank accession No. AL935325.14, wherein C is converted to G at nucleotide No. 60522.

Reference Example 19

Synthesis of HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^p$-$T^p$-$G^t$
(SEQ ID NO: 7)

HO $C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^p$-$T^p$-$G^t$ (SEQ ID NO: 7) (hereinafter referred to as "primer E") was synthesized by a common method using a nucleic acid automatic synthesizer. The nucleotide sequence of the present compound (primer E) is a sequence corresponding to nucleotide Nos. 60499-60523 described in GenBank accession No. AL935325.14, wherein C is converted to T at nucleotide No. 60522 and wherein A is converted to G at nucleotide No. 60523. This sequence is shown in SEQ ID NO: 7.

Reference Example 20

Synthesis of HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^p$-$T^p$-$A^t$
(SEQ ID NO: 8)

HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^p$-$T^p$-$A^t$ (SEQ ID NO: 8) (hereinafter referred to as "primer F") was synthesized by a common method using a nucleic acid automatic synthesizer. The nucleotide sequence of the present compound (primer F) is a sequence corresponding to nucleotide Nos. 60499-60523 described in GenBank accession No. AL935325.14, wherein C is converted to T at nucleotide No. 60522. This sequence is shown in SEQ ID NO: 8.

Reference Example 21

Synthesis of HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^p$-$G^p$-$G^t$
(SEQ ID NO: 9)

HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^p$-$G^p$-$G^t$ (SEQ ID NO: 9) (hereinafter referred to as "primer G") was synthesized by a common method using a nucleic acid automatic synthesizer.

The nucleotide sequence of primer G is a sequence corresponding to nucleotide Nos. 60499-60523 described in GenBank accession No. AL935325.14, wherein C is converted to G at nucleotide No. 60522 and wherein A is converted to G at nucleotide No. 60523. This sequence is shown in SEQ ID NO: 9.

Reference Example 22

Synthesis of HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^p$-$G^p$-$A^t$ (SEQ ID NO: 10)

HO-$C^p$-$A^p$-$T^p$-$G^p$-$T^p$-$C^p$-$T^p$-$A^p$-$C^p$-$T^p$-$G^p$-$C^p$-$T^p$-$A^p$-$C^p$-$T^p$-$T^p$-$C^p$-$A^p$-$C^p$-$A^p$-$T^p$-$G^p$-$G^p$-$A^t$ (SEQ ID NO: 10) (hereinafter referred to as "primer H") was synthesized by a common method using a nucleic acid automatic synthesizer.

The nucleotide sequence of primer H is a sequence corresponding to nucleotide Nos. 60499-60523 described in GenBank accession No. AL935325.14, wherein C is converted to G at nucleotide No. 60522. This sequence is shown in SEQ ID NO: 10.

Test example 3

Detection of SNP in Angiopoietin-Like 3 Gene Promoter

A tail tip (1.5 cm) collected from each of the mice derived from the mouse AKR strain and the KK mouse Nga strain (4-week-old) was immersed in 840 µl of a dissolving solution (consisting of 720 µl of 1×SSC, 80 µl of 10% SDS, and 40 µl of 10 mg/ml proteinase K), and it was then shaken overnight while incubating at 50° C. Subsequently, 20 µl of 1 mg/ml ribonuclease A was added to the reaction solution, and it was then incubated at 50° C. for 1 hour. Thereafter, phenol-chloroform extraction was carried out twice, and an ethanol precipitation operation was then carried out once. The precipitate was dissolved in 150 µl of a buffer comprising 10 mM Tris-HCl (pH 7.5) and 1 mM EDTA. Thereafter, the solution was subjected to spectrophotometry (U-3000, manufactured by Hitachi, Ltd.), so as to measure the absorbance at a wavelength of 260 nm. Thereafter, sterilized water was added thereto so as to adjust the concentration to 25 ng/µl, thereby preparing the genomic DNA sample.

Figure 11:
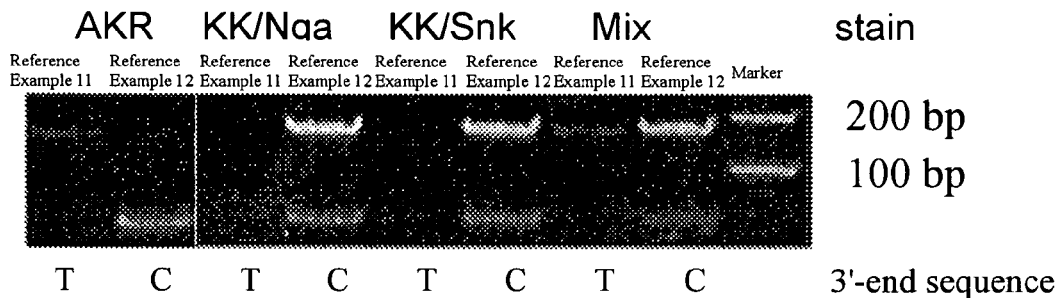
FIG. 11 is a view showing polymorphism in an angiopoietin-like 3 gene promoter.

From the results of direct sequencing, the SNP in the angiopoietin-like 3 gene promoter is as shown in FIG. 11.

The nucleotide sequence of the reverse primer is as follows: 5'-GTCACTAGACTACTGCTTACTGTCC-3' (SEQ ID NO: 6 of the sequence listing)
(The nucleotide sequence of the present compound is complementary to a sequence corresponding to nucleotide Nos. 60658-60682 described in GenBank accession No. AL935325).

5 µl of a solution was prepared from 12.5 µl of Premix Taq (manufactured by Takara Shuzo Co., Ltd.), 0.125 µl of a genomic DNA solution (100 ng/1 µl), 5 µl (1.25 µM) of the reverse primer, 2.38 µl of sterilized water, and a compound as described in any one of the examples and reference examples was used as the forward primer (primer A, B, C, D, E, F, G, or H) (1.25 µM). The prepared solution was subjected to a PCR reaction (Hot Start method), using a Takara PCR Thermal Cycler PERSONAL (TP240). As the reaction cycle, after a treatment at 94° C. for 10 minutes, a cycle consisting of 94° C., 1 minute, 63° C., 1 minute, and 72° C., 1 minute, was repeated for 30 cycles.

After completion of the reaction, 1 µl of an additive solution (loading solution) was added to 5 µl of the reaction solution, followed by 10% polyacrylamide gel electrophoresis (1×TBE, 200 V constant voltage, approximately 1 hour). Thereafter, the resultant gel was stained with SYBR Green I (manufactured by Cambrex), and the Molecular Imager FX Fluorescent Imager system (Bio-Rad) was used to visualize the band.

It was predicted that when the PCR reaction was carried out correctly, if the genomic DNA (AKR) derived from the mouse AKR strain was used, a gene (182 bp) was selectively amplified, and that if the genomic DNA (KK/Nga) derived from the KK mouse Nga strain was used, a gene (184 bp) was selectively amplified.

Figure 12:
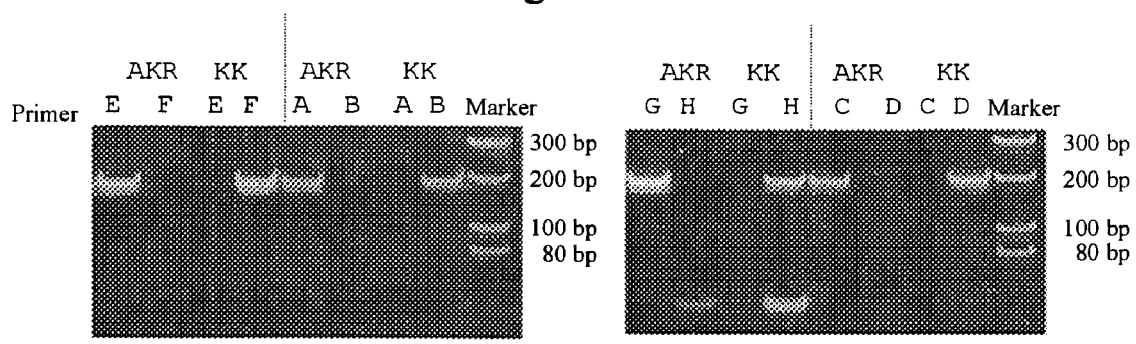
FIG. 12 is a view showing the results of PCR using Premix Taq and various types of primers.

The results are shown in FIG. 12. In the case where PCR was carried out using primer E or primer F as the forward primer, when primer E was used as the primer for the genomic DNA derived from the mouse AKR strain, amplification of a gene was confirmed. On the other hand, for the genomic DNA derived from the KK mouse Nga strain, in both cases of using primer F or primer E as the primer, amplification of a gene was observed.

Moreover, in the case where PCR was carried out using primer A or primer B as the primer, when primer A was used as the primer for genomic DNA derived from the mouse AKR strain, amplification of a gene was confirmed. On the other hand, for genomic DNA derived from the KK mouse Nga strain, when primer B was used as the primer, amplification of a gene was observed.

In the case where primer G or primer H was used as the primer, for genomic DNA derived from the mouse AKR strain, when primer G was used as the primer, a gene product of interest was amplified. When primer H was used as the primer, an amplified product was obtained, which was considered to be a by-product smaller than the size of the product of interest. In addition, for the genomic DNA derived from the KK mouse Nga strain, when primer H was used as the primer, not only a gene product of interest, but also an amplified product, which was considered to be a by-product having a smaller chain length than the size of a product of interest, was obtained.

When primer C or primer D was used as the primer, for genomic DNA derived from the mouse AKR strain, when primer C was used as the primer, a gene was amplified. Further, for genomic DNA derived from the KK mouse Nga strain, when primer D was used as the primer, amplification of a gene was observed.

From the aforementioned results, it could be confirmed that the use of a primer, wherein an ENA unit has been introduced into the third position from the 3'-end thereof, improves detection efficiency, when compared with a conventional primer.

INDUSTRIAL APPLICABILITY

The method of the present invention enables detection of gene polymorphism. In addition, using a method for detecting gene polymorphism of the present invention, it becomes possible to detect polymorphism more precisely than when a natural oligonucleotide is used.

Moreover, when an oligonucleotide for detection of gene polymorphism and a kit for detecting gene polymorphism comprising the above oligonucleotide, are used in the above methods, various types of gene polymorphism can be detected. The present invention can be used in various fields such as medicine, agriculture, food processing, or industry, but such industrial fields are not limited, as long as such fields require detection of gene polymorphism.

The invention claimed is:

1. An oligonucleotide used as a primer consisting of:
   (a) a 2'-O,4'-C-ethylene nucleotide (ENA) unit which is the third nucleotide from the 3'-end of the oligonucleotide, and the other nucleotides are natural nucleotides, wherein the nucleotide at the 3'-end is defined as the first nucleotide;
   (b) a nucleotide complementary to the reference nucleotide of a target gene at the 3'-end position thereof; and
   (c) nucleotides complementary to a nucleotide sequence of the target gene in other positions,
   or a salt thereof,
   wherein the oligonucleotide has a base length of 18 to 25 bases.

2. The oligonucleotide according to claim 1, wherein the target gene is a drug metabolizing gene.

3. The oligonucleotide according to claim 2, wherein the drug metabolizing gene is selected from the group consisting of cytochrome P4501A2, cytochrome P4502A6, cytochrome P4502C9, cytochrome P4502C19, cytochrome P4502D6 and cytochrome P4502E1.

4. The oligonucleotide according to claim 1, wherein the target gene is selected from the group consisting of thiopurine methyltransferase, N-acetyltransferase, UDP-glucuronosyltransferase and glutathione S-transferase.

5. The oligonucleotide according to claim 1, wherein the target gene is a disease-associated gene.

6. The oligonucleotide according to claim 1, wherein the target gene is selected from the group consisting of a causative gene of ulcerative colitis, a causative gene of arthritis rheumatoides, a causative gene of Alzheimer's disease, a causative gene of schizophrenia, a causative gene of manic-depressive psychosis, a causative gene of albuminuria, a causative gene of myocardial infarction and a causative gene of adiposis.

7. The oligonucleotide according to claim 1, wherein the target gene is selected from the group consisting of HLA, TCRα, APOE4, a dopamine D3 receptor, tryptophan hydroxylase, an angiotensin precursor, a blood coagulation factor VII, leptin and human prothrombin.

8. An oligonucleotide used as a primer consisting of:
(a) a 2'-O,4'-C-ethylene nucleotide (ENA) unit which is the third nucleotide from the 3'-end of the oligonucleotide, and the other nucleotides are natural nucleotides, wherein the nucleotide at the 3'-end is defined as the first nucleotide;
(b) a nucleotide complementary to the mutant nucleotide of a target gene at the 3'-end position thereof and
(c) nucleotides complementary to a nucleotide sequence of the target gene in other positions,
or a salt thereof,
wherein the oligonucleotide has a base length of 18 to 25 bases.

9. The oligonucleotide according to claim 8, wherein the target gene is a drug metabolizing gene.

10. The oligonucleotide according to claim 9, wherein the drug metabolizing gene is selected from the group consisting of cytochrome P4501A2, cytochrome P4502A6, cytochrome P4502C9, cytochrome P4502C19, cytochrome P4502D6 and cytochrome P4502E1.

11. The oligonucleotide according to claim 8, wherein the target gene is selected from the group consisting of thiopurine methyltransferase, N-acetyltransferase, UDP-glucuronosyltransferase and glutathione S-transferase.

12. The oligonucleotide according to claim 8, wherein the target gene is a disease-associated gene.

13. The oligonucleotide according to claim 8, wherein the target gene is selected from the group consisting of a causative gene of ulcerative colitis, a causative gene of arthritis rheumatoides, a causative gene of Alzheimer's disease, a causative gene of schizophrenia, a causative gene of manic-depressive psychosis, a causative gene of albuminuria, a causative gene of myocardial infarction and a causative gene of adiposis.

14. The oligonucleotide according to claim 8, wherein the target gene is selected from the group consisting of HLA, TCRα, APOE4, a dopamine D3 receptor, tryptophan hydroxylase, an angiotensin precursor, a blood coagulation factor VII, leptin and human prothrombin.

15. An oligonucleotide used as a primer consisting of:
(a) a nucleotide at the 3'-end of the oligonucleotide which is a nucleotide complementary to the reference nucleotide of a target gene;
(b) a nucleotide which is the second nucleotide from the 3'-end of the oligonucleotide, wherein the nucleotide at the 3'-end is defined as the first nucleotide, the second nucleotide is a nucleotide that is not complementary to the nucleotide of a reference gene;
(c) a region of the nucleotides complementary to a region of the target gene in other positions; and
(d) a nucleotide which is the third nucleotide from the 3'-end of the oligonucleotide is a 2'-O,4'-C-ethylene nucleotide (ENA) unit, and the other nucleotides are natural nucleotides,
or a salt thereof,
wherein the oligonucleotide has a base length of 18 to 25 bases.

16. The oligonucleotide according to claim 15, wherein the target gene is a drug metabolizing gene.

17. The oligonucleotide according to claim 16, wherein the drug metabolizing gene is selected from the group consisting of cytochrome P4501A2, cytochrome P4502A6, cytochrome P4502C9, cytochrome P4502C19, cytochrome P4502D6 and cytochrome P4502E1.

18. The oligonucleotide according to claim 15, wherein the target gene is selected from the group consisting of thiopurine methyltransferase, N-acetyltransferase, UDP-glucuronosyltransferase and glutathione S-transferase.

19. The oligonucleotide according to claim 15, wherein the target gene is a disease-associated gene.

20. The oligonucleotide according to claim 15, wherein the target gene is selected from the group consisting of ulcerative colitis, a causative gene of arthritis rheumatoides, a causative gene of Alzheimer's disease, a causative gene of schizophrenia, a causative gene of manic-depressive psychosis, a causative gene of albuminuria, a causative gene of myocardial infarction and a causative gene of adiposis.

21. The oligonucleotide according to claim 15, wherein the target gene is selected from the group consisting of HLA, TCRα, APOE4, a dopamine D3 receptor, tryptophan hydroxylase, an angiotensin precursor, a blood coagulation factor VII, leptin and human prothrombin.

22. An oligonucleotide used as a primer consisting of:
(a) a nucleotide at the 3'-end of the oligonucleotide which is a nucleotide complementary to the mutant nucleotide of a target gene;
(b) a nucleotide which is the second nucleotide from the 3'-end of the nucleotide, wherein the nucleotide at the 3'-end is defined as the first nucleotide, the second nucleotide is a nucleotide that is not complementary to the nucleotide of a reference gene;
(c) a region of the nucleotides complementary to a region of the target gene in the other positions; and
(d) a nucleotide which is the third nucleotide from the 3'-end of the oligonucleotide is a 2'-O,4'-C-ethylene nucleotide (ENA) unit, and the other nucleotides are natural nucleotides,
or a salt thereof,
wherein the oligonucleotide has a base length of 18 to 25 bases.

23. The oligonucleotide according to claim 22, wherein the target gene is a drug metabolizing gene.

24. The oligonucleotide according to claim 21, wherein the drug metabolizing gene is selected from the group consisting of cytochrome P4501A2, cytochrome P4502A6, cytochrome P4502C9, cytochrome P4502C19, ccytochrome P4502D6 and cytochrome P4502E1.

25. The oligonucleotide according to claim 22, wherein the target gene is selected from the group consisting of thiopurine, methyltransferase, N-acetyltransferase, UDP-glucuronosyltransferase and glutathione S-transferase.

26. The oligonucleotide according to claim 22, wherein the target gene is a disease-associated gene.

27. The oligonucleotide according to claim 22, wherein the target gene is selected from the group consisting of a causative gene of ulcerative colitis, a causative gene of arthritis rheumatoides, a causative gene of Alzheimer's disease, a causative gene of schizophrenia, a causative gene of manic-depressive psychosis, a causative gene of albuminuria, a causative gene of myocardial infarction and a causative gene of adiposis.

28. The oligonucleotide according to claim 22, wherein the target gene is selected from the group consisting of HLA, TCRα, APOE4, a dopamine D3 receptor, tryptophan hydroxylase, an angiotensin precursor, a blood coagulation factor VII, leptin and human prothrombin.

29. A method for detecting gene polymorphism comprising:
(a) performing a PCR with a template nucleic acid of a target gene comprising a genetically polymorphic sequence, said PCR being carried out with a first oligonucleotide which is an oligonucleotide according to any one of claims 1 to 22 and a second oligonucleotide capable of amplifying a sequence of interest together with said first oligonucleotide in the PCR; and
(b) determining the presence or absence of gene polymorphism in the nucleic acid based on whether or not a reaction product is generated in step (a).

30. The method according to claim 29, wherein the determining of whether or not a reaction product is generated is carried out by at least one method selected from the group consisting of electrophoresis, TAQMAN® PCR and MALDI-TOF/MS.

31. The method according to claim 29, wherein the gene polymorphism is a single nucleotide polymorphism.

32. A method for determining the nucleotide sequence of a genetically polymorphic sequence comprising:
(a) performing a PCR with a template nucleic acid of a target gene comprising a genetically polymorphic sequence, said PCR being carried out with a first oligonucleotide which is an oligonucleotide according to any one of claims 1 to 22 and a second oligonucleotide capable of amplifying the sequence of interest together with said first oligonucleotide in the PCR; and
(b) determining the nucleotide sequence of a genetically polymorphic sequence in the nucleic acid based on whether or not a reaction product is generated in step (a).

33. The method according to claim 32, wherein the determining of whether or not a reaction product is generated is carried out by at least one method selected from the group consisting of electrophoresis, TAQMAN® PCR and MALDI-TOF/MS.

34. The method according to claim 30, wherein the gene polymorphism is a single nucleotide polymorphism.

35. A kit for detecting gene polymorphism comprising:
(a) a first oligonucleotide having the following characteristics (i) to (iii):
(i) the third nucleotide from the 3'-end of the first oligonucleotide is a 2'-O,4'-C-ethylene nucleotide (ENA) unit, and the other nucleotides are natural nucleotides, wherein the nucleotide at the 3'-end is defined as the first nucleotide;
(ii) the 3'-end nucleotide of the first oligonucleotide is a nucleotide complementary to a reference nucleotide of a target gene; and
(iii) the first oligonucleotide has a region of the nucleotides complementary to a region of the target gene in other positions;
(b) a second oligonucleotide capable of amplifying a sequence of interest in the target gene, together with the first oligonucleotide set forth in (a) above;
(c) DNA polymerase; and
(d) a PCR buffer,
wherein the first oligonucleotide and the second oligonucleotide have a base length of 18 to 25 bases.

36. A kit for detecting gene polymorphism comprising:
(a) a first oligonucleotide having the following characteristics (i) to (iii):
(i) the third nucleotide from the 3'-end of the first oligonucleotide is a 2'-O,4'-C-ethylene nucleotide (ENA) unit, and the other nucleotides are natural nucleotides, wherein the nucleotide at the 3'-end is defined as the first nucleotide;
(ii) the 3'-end nucleotide of the first oligonucleotide is complementary to a mutant nucleotide of a target gene; and
(iii) the first oligonucleotide has a region of the nucleotides complementary to a region of the target gene in other positions;
(b) a primer capable of amplifying a sequence of interest in the target gene, together with the oligonucleotide set forth in (a) above;
(c) DNA polymerase; and
(d) a PCR buffer,
wherein the oligonucleotide has a base length of 18 to 25 bases.

37. A kit for detecting gene polymorphism comprising:
(a) a first oligonucleotide having the following characteristics (i) to (iii):
(i) the third nucleotide from the 3'-end of the first oligonucleotide is a 2'-O,4'-C-ethylene nucleotide (ENA) unit, and the other nucleotides are natural nucleotides, wherein the nucleotide at the 3'-end is defined as the first nucleotide;
(ii) the 3'-end nucleotide of the first oligonucleotide is a nucleotide complementary to a reference nucleotide of a target gene; and
(iii) the first oligonucleotide has a region of the nucleotides which is complementary to a region of the target gene in other positions;
(b) a second oligonucleotide having the following characteristics (i) to (iii):
(i) the third nucleotide from the 3'-end of the second oligonucleotide is a 2'-O,4'-C-ethylene nucleotide (ENA) unit and the other nucleotides are natural nucleotides;
(ii) the 3'-end nucleotide of the second oligonucleotide is complementary to a mutant nucleotide of a target gene;
(iii) the second oligonucleotide has a region of the nucleotides which is complementary to a region of the target gene in the other positions;
(c) a third oligonucleotide capable of amplifying a sequence of interest in the target gene, together with the first oligonucleotide set forth in (a) above or the second oligonucleotide set forth in (b) above;
(d) DNA polymerase; and
(e) a PCR buffer,
wherein the first oligonucleotide, the second oligonucleotide and the third oligonucleotide have a base length of 18 to 25 bases.

38. A kit for detecting gene polymorphism comprising:
(a) a first oligonucleotide having the following characteristics (i) to (iv):
(i) the 3'-end nucleotide of the first oligonucleotide is a nucleotide complementary to a reference nucleotide of a target gene;

(ii) the second nucleotide from the 3'-end of the oligonucleotide, wherein the nucleotide at the 3'-end is defined as the first nucleotide, the second nucleotide is a nucleotide that is not complementary to the nucleotide of a reference gene;
(iii) the first oligonucleotide has a region of nucleotides complementary to a region of the target gene in the other positions; and
(iv) the third nucleotide from the 3'-end of the first oligonucleotide is a 2'-O,4'-C-ethylene nucleotide (ENA) unit, and the other nucleotides are natural nucleotides,
or a salt thereof;
(b) a second oligonucleotide capable of amplifying a sequence of interest in the target gene, together with the first oligonucleotide set forth in (a) above;
(c) DNA polymerase; and
(d) a PCR buffer,
wherein the first oligonucleotide and the second oligonucleotide have a base length of 18 to 25 bases.

39. A kit for detecting gene polymorphism comprising:
(a) a first oligonucleotide having the following characteristics (i) to (iv):
(i) the 3'-end nucleotide of the first oligonucleotide is a nucleotide complementary to a mutant nucleotide of a target gene;
(ii) the second nucleotide from the 3'-end of the first oligonucleotide, wherein the nucleotide at the 3'-end is defined as the first nucleotide, the second nucleotide is a nucleotide that is not complementary to a nucleotide of a reference gene;
(iii) the first oligonucleotide has a region of nucleotides complementary to a region of the target gene in the other positions; and
(iv) the third nucleotide from the 3'-end thereof is a 2'-O,4'-C-ethylene nucleotide (ENA) unit, and the other nucleotides are natural nucleotides;
or a salt thereof;
(b) a second oligonucleotide capable of amplifying a sequence of interest in the target gene, together with the first oligonucleotide set forth in (a) above;
(c) DNA polymerase; and
(d) a PCR buffer,
wherein the first oligonucleotide and the second oligonucleotide have a base length of 18 to 25 bases.

40. A kit for detecting gene polymorphism comprising:
(a) a first oligonucleotide having the following characteristics (i) to (iv):
(i) the 3'-end nucleotide of the first oligonucleotide is a nucleotide complementary to a reference nucleotide of a target gene;
(ii) the second nucleotide from the 3'-end of the first oligonucleotide, wherein the nucleotide at the 3'-end is defined as the first nucleotide, the second nucleotide is a nucleotide that is not complementary to a nucleotide of a reference gene;
(iii) the first oligonucleotide has a region of nucleotides complementary to a region of the target gene in the other positions; and
(iv) the third nucleotide from the 3'-end thereof is a 2'-O,4'-C-ethylene nucleotide (ENA) unit, and the other nucleotides are natural nucleotides, or a salt thereof;
(b) a second oligonucleotide having the following characteristics (i) to (iv):
(i) the 3'-end nucleotide of the second oligonucleotide is a nucleotide complementary to a mutant nucleotide of a target gene;
(ii) the second nucleotide from the 3'-end of the second oligonucleotide, wherein the nucleotide at the 3'-end is defined as the first nucleotide, the second nucleotide is a nucleotide that is not complementary to a nucleotide of a reference gene;
(iii) the second oligonucleotide has nucleotides complementary to the nucleotides of the target gene in the other positions; and
(iv) the third nucleotide from the 3'-end thereof is a 2'-O,4'-C-ethylene nucleotide (ENA) unit, and the other nucleotides are natural nucleotides,
or a salt thereof;
(c) a third oligonucleotide capable of amplifying a sequence of interest in the target gene, together with the first oligonucleotide set forth in (a) above or the second oligonucleotide set forth in (b) above;
(d) DNA polymerase; and
(e) a PCR buffer,
wherein the first oligonucleotide, the second oligonucleotide and the third oligonucleotide have a base length of 18 to 25 bases.

41. The kit according to any one of claims 35 to 40, wherein the gene polymorphism is a single nucleotide polymorphism.

* * * * *

UNITED STATES PATENT AND TRADEMARK OFFICE
CERTIFICATE OF CORRECTION

| | | |
|---|---|---|
| PATENT NO. | : 7,906,639 B2 | Page 1 of 1 |
| APPLICATION NO. | : 10/577982 | |
| DATED | : March 15, 2011 | |
| INVENTOR(S) | : Koizumi | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 95 days.

Signed and Sealed this

Nineteenth Day of July, 2011

David J. Kappos
*Director of the United States Patent and Trademark Office*

SEQUENCE LISTING

<160> NUMBER OF SEQ ID NOS: 32

<210> SEQ ID NO 1
<211> LENGTH: 20
<212> TYPE: DNA
<213> ORGANISM: Homo sapiens

<400> SEQUENCE: 1
cactgggagc attgaggctc                                               20

<210> SEQ ID NO 2
<211> LENGTH: 20
<212> TYPE: DNA
<213> ORGANISM: Homo sapiens
<220> FEATURE:
<221> NAME/KEY: allele
<222> LOCATION: (20)..(20)
<223> OTHER INFORMATION: C is transitioned to T

<400> SEQUENCE: 2
cactgggagc attgaggctt                                               20

<210> SEQ ID NO 3
<211> LENGTH: 28
<212> TYPE: DNA
<213> ORGANISM: Mus musculus
<220> FEATURE:
<221> NAME/KEY: allele
<222> LOCATION: (28)..(28)
<223> OTHER INFORMATION: C is transitioned to T

<400> SEQUENCE: 3
atctgtctac atatatatac acacacat                                      28

<210> SEQ ID NO 4
<211> LENGTH: 28
<212> TYPE: DNA
<213> ORGANISM: Mus musculus

<400> SEQUENCE: 4
atctgtctac atatatatac acacacac                                      28

<210> SEQ ID NO 5
<211> LENGTH: 18
<212> TYPE: DNA
<213> ORGANISM: Homo sapiens

<400> SEQUENCE: 5
gggtgaaggc tgtgaccg                                                 18

<210> SEQ ID NO 6
<211> LENGTH: 25
<212> TYPE: DNA
<213> ORGANISM: Mus musculus

<400> SEQUENCE: 6
gtcactagac tactgcttac tgtcc                                         25

<210> SEQ ID NO 7
<211> LENGTH: 25
<212> TYPE: DNA
<213> ORGANISM: Artificial Sequence
<220> FEATURE:
<223> OTHER INFORMATION: primerE

```
<400> SEQUENCE: 7
catgtctact gctacttcac atgtg                                      25

<210> SEQ ID NO 8
<211> LENGTH: 25
<212> TYPE: DNA
<213> ORGANISM: Artificial Sequence
<220> FEATURE:
<223> OTHER INFORMATION: primer F

<400> SEQUENCE: 8
catgtctact gctacttcac atgta                                      25

<210> SEQ ID NO 9
<211> LENGTH: 25
<212> TYPE: DNA
<213> ORGANISM: Artificial Sequence
<220> FEATURE:
<223> OTHER INFORMATION: primer G

<400> SEQUENCE: 9
catgtctact gctacttcac atggg                                      25

<210> SEQ ID NO 10
<211> LENGTH: 25
<212> TYPE: DNA
<213> ORGANISM: Artificial Sequence
<220> FEATURE:
<223> OTHER INFORMATION: primer H

<400> SEQUENCE: 10
catgtctact gctacttcac atgga                                      25

<210> SEQ ID NO 11
<211> LENGTH: 20
<212> TYPE: DNA
<213> ORGANISM: Homo sapiens
<220> FEATURE:
<221> NAME/KEY: modified_base
<222> LOCATION: (18)..(18)
<223> OTHER INFORMATION: 2'-O,4'-C-ethylene nucleotide

<400> SEQUENCE: 11
cactgggagc attgaggctc                                            20

<210> SEQ ID NO 12
<211> LENGTH: 20
<212> TYPE: DNA
<213> ORGANISM: Homo sapiens
<220> FEATURE:
<221> NAME/KEY: modified_base
<222> LOCATION: (18)..(18)
<223> OTHER INFORMATION: 2'-O,4'-C-ethylene nucleotide

<400> SEQUENCE: 12
cactgggagc attgaggctt                                            20

<210> SEQ ID NO 13
<211> LENGTH: 28
<212> TYPE: DNA
<213> ORGANISM: Mus musculus
<220> FEATURE:
<221> NAME/KEY: modified_base
<222> LOCATION: (26)..(26)
<223> OTHER INFORMATION: 2'-O,4'-C-ethylene nucleotide
<220> FEATURE:
<221> NAME/KEY: allele
<222> LOCATION: (28)..(28)
```

```
<223> OTHER INFORMATION: C is transitioned to T

<400> SEQUENCE: 13
atctgtctac atatatatac acacacat                                              28

<210> SEQ ID NO 14
<211> LENGTH: 28
<212> TYPE: DNA
<213> ORGANISM: Mus musculus
<220> FEATURE:
<221> NAME/KEY: modified_base
<222> LOCATION: (26)..(26)
<223> OTHER INFORMATION: 2'-O,4'-C-ethylene nucleotide

<400> SEQUENCE: 14
atctgtctac atatatatac acacacac                                              28

<210> SEQ ID NO 15
<211> LENGTH: 20
<212> TYPE: DNA
<213> ORGANISM: Homo sapiens
<220> FEATURE:
<221> NAME/KEY: modified_base
<222> LOCATION: (20)..(20)
<223> OTHER INFORMATION: 2'-O,4'-ethylene nucleoside

<400> SEQUENCE: 15
cactgggagc attgaggctc                                                       20

<210> SEQ ID NO 16
<211> LENGTH: 20
<212> TYPE: DNA
<213> ORGANISM: Homo sapiens
<220> FEATURE:
<221> NAME/KEY: allele
<222> LOCATION: (20)..(20)
<223> OTHER INFORMATION: C is transitioned to T
<220> FEATURE:
<221> NAME/KEY: modified_base
<222> LOCATION: (20)..(20)
<223> OTHER INFORMATION: 2'-O,4'-C-ethylene nucleoside

<400> SEQUENCE: 16
cactgggagc attgaggctt                                                       20

<210> SEQ ID NO 17
<211> LENGTH: 20
<212> TYPE: DNA
<213> ORGANISM: Homo sapiens
<220> FEATURE:
<221> NAME/KEY: modified_base
<222> LOCATION: (19)..(19)
<223> OTHER INFORMATION: 2'-O,4'-C-ethylene nucleotide

<400> SEQUENCE: 17
cactgggagc attgaggctc                                                       20

<210> SEQ ID NO 18
<211> LENGTH: 20
<212> TYPE: DNA
<213> ORGANISM: Homo sapiens
<220> FEATURE:
<221> NAME/KEY: modified_base
<222> LOCATION: (19)..(19)
<223> OTHER INFORMATION: 2'-O,4'-C-ethylene nucleotide
<220> FEATURE:
<221> NAME/KEY: allele
<222> LOCATION: (20)..(20)
<223> OTHER INFORMATION: C is transitioned to T
```

```
<400> SEQUENCE: 18
cactgggagc attgaggctt                                                20

<210> SEQ ID NO 19
<211> LENGTH: 20
<212> TYPE: DNA
<213> ORGANISM: Homo sapiens
<220> FEATURE:
<221> NAME/KEY: modified_base
<222> LOCATION: (17)..(17)
<223> OTHER INFORMATION: 2'-O,4'-C-ethylene nucleotide

<400> SEQUENCE: 19
cactgggagc attgaggctc                                                20

<210> SEQ ID NO 20
<211> LENGTH: 20
<212> TYPE: DNA
<213> ORGANISM: Homo sapiens
<220> FEATURE:
<221> NAME/KEY: modified_base
<222> LOCATION: (17)..(17)
<223> OTHER INFORMATION: 2'-O,4'-C-ethylene nucleotide
<220> FEATURE:
<221> NAME/KEY: allele
<222> LOCATION: (20)..(20)
<223> OTHER INFORMATION: C is transitioned to T

<400> SEQUENCE: 20
cactgggagc attgaggctt                                                20

<210> SEQ ID NO 21
<211> LENGTH: 20
<212> TYPE: DNA
<213> ORGANISM: Homo sapiens
<220> FEATURE:
<221> NAME/KEY: modified_base
<222> LOCATION: (18)..(18)
<223> OTHER INFORMATION: 2'-O,4'-C-methylene nucleotide

<400> SEQUENCE: 21
cactgggagc attgaggctc                                                20

<210> SEQ ID NO 22
<211> LENGTH: 20
<212> TYPE: DNA
<213> ORGANISM: Homo sapiens
<220> FEATURE:
<221> NAME/KEY: modified_base
<222> LOCATION: (18)..(18)
<223> OTHER INFORMATION: 2'-O,4'-C-methylene nucleotide
<220> FEATURE:
<221> NAME/KEY: allele
<222> LOCATION: (20)..(20)
<223> OTHER INFORMATION: C is transitioned to T

<400> SEQUENCE: 22
cactgggagc attgaggctt                                                20

<210> SEQ ID NO 23
<211> LENGTH: 28
<212> TYPE: DNA
<213> ORGANISM: Mus musculus
<220> FEATURE:
<221> NAME/KEY: allele
<222> LOCATION: (28)..(28)
<223> OTHER INFORMATION: C is transitioned to T
<220> FEATURE:
<221> NAME/KEY: modified_base
<222> LOCATION: (28)..(28)
```

-continued

```
<223> OTHER INFORMATION: 2'-O,4'-C-ethylene nucleoside

<400> SEQUENCE: 23
atctgtctac atatatatac acacacat                                              28

<210> SEQ ID NO 24
<211> LENGTH: 28
<212> TYPE: DNA
<213> ORGANISM: Mus musculus
<220> FEATURE:
<221> NAME/KEY: modified_base
<222> LOCATION: (28)..(28)
<223> OTHER INFORMATION: 2'-O,4'-C-ethylene nucleoside

<400> SEQUENCE: 24
atctgtctac atatatatac acacacac                                              28

<210> SEQ ID NO 25
<211> LENGTH: 28
<212> TYPE: DNA
<213> ORGANISM: Mus musculus
<220> FEATURE:
<221> NAME/KEY: modified_base
<222> LOCATION: (27)..(27)
<223> OTHER INFORMATION: 2'-O,4'-C-ethylene nucleotide
<220> FEATURE:
<221> NAME/KEY: allele
<222> LOCATION: (28)..(28)
<223> OTHER INFORMATION: C is transitioned to T

<400> SEQUENCE: 25
atctgtctac atatatatac acacacat                                              28

<210> SEQ ID NO 26
<211> LENGTH: 28
<212> TYPE: DNA
<213> ORGANISM: Mus musculus
<220> FEATURE:
<221> NAME/KEY: modified_base
<222> LOCATION: (27)..(27)
<223> OTHER INFORMATION: 2'-O,4'-C-ethylene nucleotide

<400> SEQUENCE: 26
atctgtctac atatatatac acacacac                                              28

<210> SEQ ID NO 27
<211> LENGTH: 28
<212> TYPE: DNA
<213> ORGANISM: Mus musculus
<220> FEATURE:
<221> NAME/KEY: modified_base
<222> LOCATION: (25)..(25)
<223> OTHER INFORMATION: 2'-O,4'-C-ethylene nucleotide
<220> FEATURE:
<221> NAME/KEY: allele
<222> LOCATION: (28)..(28)
<223> OTHER INFORMATION: C is transitioned to T

<400> SEQUENCE: 27
atctgtctac atatatatac acacacat                                              28

<210> SEQ ID NO 28
<211> LENGTH: 28
<212> TYPE: DNA
<213> ORGANISM: Mus musculus
<220> FEATURE:
<221> NAME/KEY: modified_base
<222> LOCATION: (25)..(25)
<223> OTHER INFORMATION: 2'-O,4'-C-ethylene nucleotide
```

```
<400> SEQUENCE: 28
atctgtctac atatatatac acacacac                              28

<210> SEQ ID NO 29
<211> LENGTH: 25
<212> TYPE: DNA
<213> ORGANISM: Artificial Sequence
<220> FEATURE:
<223> OTHER INFORMATION: Primer A
<220> FEATURE:
<221> NAME/KEY: modified_base
<222> LOCATION: (23)..(23)
<223> OTHER INFORMATION: 2'-O,4'-C-ethylene nucleotide

<400> SEQUENCE: 29
catgtctact gctacttcac atgtg                                 25

<210> SEQ ID NO 30
<211> LENGTH: 25
<212> TYPE: DNA
<213> ORGANISM: Artificial Sequence
<220> FEATURE:
<223> OTHER INFORMATION: Primer B
<220> FEATURE:
<221> NAME/KEY: modified_base
<222> LOCATION: (23)..(23)
<223> OTHER INFORMATION: 2'-O,4'-C-ethylene nucleotide

<400> SEQUENCE: 30
catgtctact gctacttcac atgta                                 25

<210> SEQ ID NO 31
<211> LENGTH: 25
<212> TYPE: DNA
<213> ORGANISM: Artificial Sequence
<220> FEATURE:
<223> OTHER INFORMATION: Primer C
<220> FEATURE:
<221> NAME/KEY: modified_base
<222> LOCATION: (23)..(23)
<223> OTHER INFORMATION: 2'-O,4'-C-ethylene nucleotide

<400> SEQUENCE: 31
catgtctact gctacttcac atggg                                 25

<210> SEQ ID NO 32
<211> LENGTH: 25
<212> TYPE: DNA
<213> ORGANISM: Artificial Sequence
<220> FEATURE:
<223> OTHER INFORMATION: Primer D
<220> FEATURE:
<221> NAME/KEY: modified_base
<222> LOCATION: (23)..(23)
<223> OTHER INFORMATION: 2'-O,4'-C-ethylene-nucleotide

<400> SEQUENCE: 32
catgtctact gctacttcac atgga                                 25
```